United States Patent [19]

McLean et al.

[11] Patent Number: 5,683,982

[45] Date of Patent: *Nov. 4, 1997

[54] SYNTHETIC LUNG SURFACTANT HAVING ANTIOXIDANT PROPERTIES

[75] Inventors: Larry R. McLean, Cincinnati, Ohio; Marguerite H. Payne, Madison, Wis.

[73] Assignee: Merrell Pharmaceuticals Inc., Cincinnati, Ohio

[*] Notice: The term of this patent shall not extend beyond the expiration date of Pat. No. 5,272,252.

[21] Appl. No.: 450,427

[22] Filed: May 25, 1995

Related U.S. Application Data

[63] Continuation of Ser. No. 245,056, May 17, 1994, abandoned, which is a continuation of Ser. No. 49,014, Apr. 16, 1993, abandoned, which is a division of Ser. No. 789,918, Nov. 4, 1991, Pat. No. 5,272,252.

[51] Int. Cl.$^6$ .................................................. A61K 38/16
[52] U.S. Cl. .................. 514/12; 514/13; 514/14; 514/15; 514/16; 530/324; 530/325; 530/326; 530/327; 530/328; 530/345
[58] Field of Search ............... 514/12–16; 530/324–328, 530/345

[56] References Cited

U.S. PATENT DOCUMENTS

| | | | |
|---|---|---|---|
| 4,643,988 | 2/1987 | Segrest et al. | 514/12 |
| 4,659,805 | 4/1987 | Schilling et al. | 530/350 |
| 4,705,684 | 11/1987 | Beachey | 424/88 |
| 4,765,987 | 8/1988 | Bonte et al. | 424/450 |
| 4,861,756 | 8/1989 | Jackson | 514/11 |
| 4,882,422 | 11/1989 | Taeusch et al. | 530/350 |
| 4,912,038 | 3/1990 | Schilling et al. | 435/69.1 |
| 4,918,161 | 4/1990 | Steinbrink et al. | 530/300 |
| 5,055,553 | 10/1991 | Jacobs et al. | 530/300 |
| 5,114,921 | 5/1992 | Zasloff | 514/12 |
| 5,134,129 | 7/1992 | Lichtenberger | 514/547 |
| 5,272,252 | 12/1993 | McLean et al. | 530/327 |

FOREIGN PATENT DOCUMENTS

| | | |
|---|---|---|
| 0348967 | 6/1989 | European Pat. Off. . |
| 0368823 | 10/1989 | European Pat. Off. . |
| 0458167 | 5/1991 | European Pat. Off. . |
| 8706588 | 11/1987 | WIPO . |
| 8706943 | 11/1987 | WIPO . |
| 8803170 | 5/1988 | WIPO . |
| 8804324 | 6/1988 | WIPO . |
| 8900167 | 1/1989 | WIPO . |
| 8904326 | 5/1989 | WIPO . |
| 8906657 | 7/1989 | WIPO . |
| 9007469 | 7/1990 | WIPO . |
| 9011768 | 10/1990 | WIPO . |
| 9118015 | 11/1991 | WIPO . |

OTHER PUBLICATIONS

Nohara, et al, Eur. J. Respir. Dis. 69, pp. 321–335, (1986).
Kwong, et al, Pediatrics, vol. 76, No. 4, pp. 585–591 (1985).
Enhorning, et al, Pediatrics, vol. 76, No. 2, pp. 145–153, (1985).
Shapiro, et al, Pediatrics, Vo.. 76, No. 4, pp. 593–599, (1985).
Gitlin, et al, Pediatrics, vol. 79, No. 1, pp. 31–37, (1987).
Raju, et al, The Lancet, Mar. 21, 1987, pp. 651656.
Halliday, et al, The Lancet, Mar. 3, 1984, pp. 476–478.
British Medical Journal, vol. 294, 18 Apr. 1987, pp. 991–996.
Wilkinson, et al, The Lancet, Aug. 10, 1985, pp. 287–291.
Lachmann, et al, Adv. Exp. Med. Biol. 222:511–517, (1988).
Van Golde, et al, Physiological Reviews, vol. 68, No. 2, Apr. 1988.
Fukushima, et al, Journal of Biological Chemistry, vol. 255, No. 22, pp. 10651–10657, (1980).
Peptides, Structure and Function, Proceedings of the Ninth American Peptide Symposium.
Kaiser, Protein Engineering, pp. 193–199, (1987).
Eisenberg et al, *Proteins, Structure, Function, and Genetics* 1:16–22, (1986).
Epand, et al, *Journal of Biological Chemistry*, vol. 262, No. 19, pp. 9389–9396 (1987).
Chung et al., *Journal of Biological Chemistry*, vol. 260, No. 18, pp. 10256–10262, (1985).
Segrest et al, *Journal of Biological Chemistry*, vol. 258, No. 4, pp. 2290–2295, (1983).
Fukushima et al, *Journal of The American Chemical Society*, 101:13/Jun. 20, 1989.
Yokoyama, et al, *Journal of Biological Chemistry*, vol. 256, No. 15, pp. 7333–7339, (1980).
Fukushima, et al, *Proc. Natl. Acad. Sci. USA*, vol. 78, No. 5, pp. 2732–2736.
Kanellis, et al, *Journal of Biological Chemistry*, vol. 255, No. 23, pp. 11464–11472, (1980).
McLean, Biochemica et Biophysica Acta, 1166, 31–38 (1993).
Regan, et al, Science, vol. 241, pp. 976–978 (1991).
Morley, et al, The Lanet, Jan. 10, 1981, pp. 64–70.
White, et al, Nature, vol. 317, 26 Sep. 1985.
Krstenansky, et al, Presentation at Twelfth American Peptide Symposium at M.I.T., Cambridge MA, (1991).
McLean et al, Presentation at Biophysical Society Annual Meeting, Cincinnati, Ohio (1989).
"Porcine Lung Surfactant in RDS" Scrip No. 1312, p. 31, May 27, 1988.
Derwent Abstract 89–182812/25 (JO 1121299-A).
Lubman, R.L. et al, Am. J. of Physiology: Lung Cellular and Molecular Physiology, No. 1, Jan. 1992, pp. L292–L300.

(List continued on next page.)

*Primary Examiner*—Cecilia J. Tsang
*Assistant Examiner*—David Lukton
*Attorney, Agent, or Firm*—William R. Boudreaux

[57] ABSTRACT

Synthetic pulmonary surfactants having antioxidant properties consisting of a complex of a polypeptide, with an antioxidant moiety, having an alpha-helical structure and a lipid consisting of one or more of the lipids associated with natural pulmonary surfactant were prepared. These surfactants are useful in the treatment of respiratory distress syndrome.

16 Claims, 5 Drawing Sheets

OTHER PUBLICATIONS

Kaiser, et al, Proc. Natl. Acad. Sci., USA, vol. 80, pp. 1137–1143, (1983).

McLean, et al, Biochemistry, 30, 31–37, (1991).

Anantharmaiah, et al, *Protides Biol. Fluids*, 34; pp. 63–66, (1986).

McLean, et al, SPIE, vol. 909, Time–Resolved Laser Spectroscopy in Biochemistry, (1988).

Krstenansky, et al, FEB, vol. 242, No. 2, pp. 409–413, (1989).

Fujiwara et al, The Lancet, Sat. 12 Jan. 1980, pp. 55–59.

Dull, Drug Intelligence and Clinical Pharmacology, vol. 22, pp. 402–402, (1988).

Heffner, et al, Am. Rev. Respir. Dis. 140:531–554, (1989).

Travis, Am. Rev. Respir. Dis., 135:773–774 (1987).

Burton et al, J. Am. Chem. Soc., vol. 10, No. 24, 7053–7065, (1985).

McLean, et al, Am. Rev. Respir. Dis. vol. 147, pp. 462–465, (1993).

WMAP10

HBB - Lys - MAP10

HBS - Cys - MAP10

Trl - MAP10

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Xaa Leu Glu Lys Leu Leu Glu Xaa Leu Xaa
1               5                   10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Xaa Leu Glu Lys Leu Leu Glu Xaa Leu Xaa
1               5                   10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Leu Leu Xaa Xaa Leu Leu Xaa Xaa Leu Xaa
1               5                   10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Xaa Leu Xaa Xaa Leu Leu Xaa Xaa Leu Xaa
1               5                   10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Xaa Leu Glu Lys Leu Leu Glu Xaa Leu Xaa
1               5                   10
```

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Leu Leu Xaa Xaa Leu Leu Xaa Xaa Leu Xaa
```

```
           1                  5                        10
```

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:7:

```
Leu  Leu  Xaa  Xaa  Leu  Leu  Xaa  Xaa  Leu  Xaa
1                 5                        10
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:8:

```
Xaa  Leu  Xaa  Xaa  Leu  Leu  Xaa  Cys  Leu  Xaa
1                 5                        10
```

(2) INFORMATION FOR SEQ ID NO:9:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:9:

```
Xaa  Leu  Glu  Lys  Leu  Leu  Glu  Cys  Leu  Xaa
1                 5                        10
```

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:10:

```
Xaa  Leu  Glu  Lys  Leu  Leu  Glu  Lys  Leu  Xaa
1                 5                        10
```

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:11:

```
Leu  Leu  Xaa  Xaa  Leu  Leu  Xaa  Xaa  Leu  Xaa
1                 5                        10
```

(2) INFORMATION FOR SEQ ID NO:12:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:12:

```
Xaa  Leu  Xaa  Xaa  Leu  Leu  Xaa  Xaa  Leu  Xaa
1                  5                        10
```

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Xaa  Leu  Glu  Lys  Leu  Leu  Glu  Leu  Lys  Xaa
1                  5                        10
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Leu  Leu  Xaa  Xaa  Leu  Leu  Xaa  Xaa  Leu  Xaa
1                  5                        10
```

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Xaa  Leu  Xaa  Xaa  Leu  Leu  Xaa  Xaa  Leu  Xaa
1                  5                        10
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Xaa  Leu  Xaa  Xaa  Leu  Leu  Xaa  Xaa  Leu  Xaa
1                  5                        10
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Xaa Leu Glu Lys Leu Leu Glu Lys Leu Xaa
1               5                   10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Leu Leu Xaa Xaa Leu Leu Xaa Xaa Leu Xaa
1               5                   10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Xaa Leu Xaa Xaa Leu Leu Xaa Xaa Leu Xaa
1               5                   10
```

( 2 ) INFORMATION FOR SEQ ID NO:20:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

```
Xaa Leu Glu Lys Leu Leu Glu Xaa Leu Xaa
1               5                   10
```

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Leu Leu Xaa Xaa Leu Leu Xaa Xaa Leu Xaa
1               5                   10
```

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Xaa Leu Xaa Xaa Leu Leu Xaa Xaa Leu Xaa
```

(2) INFORMATION FOR SEQ ID NO:23:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:23:

```
Xaa  Leu  Glu  Lys  Leu  Leu  Glu  Xaa  Leu  Xaa
 1                 5                           10
```

(2) INFORMATION FOR SEQ ID NO:24:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:24:

```
Leu  Leu  Xaa  Xaa  Leu  Leu  Xaa  Xaa  Leu  Xaa
 1                 5                           10
```

(2) INFORMATION FOR SEQ ID NO:25:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:25:

```
Xaa  Leu  Xaa  Xaa  Leu  Leu  Xaa  Xaa  Leu  Xaa
 1                 5                           10
```

(2) INFORMATION FOR SEQ ID NO:26:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:26:

```
Xaa  Leu  Xaa  Xaa  Leu  Leu  Xaa  Cys  Leu  Xaa
 1                 5                           10
```

(2) INFORMATION FOR SEQ ID NO:27:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:27:

```
Xaa  Leu  Xaa  Xaa  Leu  Leu  Xaa  Xaa  Leu  Xaa
 1                 5                           10
```

(2) INFORMATION FOR SEQ ID NO:28:

( i ) SEQUENCE CHARACTERISTICS:
     ( A ) LENGTH: 10 amino acids
     ( B ) TYPE: amino acid
     ( D ) TOPOLOGY: linear ( i i ) MOLECULE TYPE: peptide ( x i ) SEQUENCE DESCRIPTION: SEQ ID NO:28:

Xaa Leu Glu Lys Leu Leu Glu Xaa Leu Xaa
 1               5                   10

( 2 ) INFORMATION FOR SEQ ID NO:29:

( i ) SEQUENCE CHARACTERISTICS:
          ( A ) LENGTH: 10 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:29:

Xaa Leu Glu Lys Leu Leu Glu Xaa Leu Xaa
 1               5                   10

( 2 ) INFORMATION FOR SEQ ID NO:30:

( i ) SEQUENCE CHARACTERISTICS:
          ( A ) LENGTH: 10 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:30:

Xaa Leu Glu Lys Leu Leu Glu Xaa Leu Xaa
 1               5                   10

( 2 ) INFORMATION FOR SEQ ID NO:31:

( i ) SEQUENCE CHARACTERISTICS:
          ( A ) LENGTH: 10 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:31:

Xaa Leu Glu Lys Leu Leu Glu Xaa Leu Xaa
 1               5                   10

( 2 ) INFORMATION FOR SEQ ID NO:32:

( i ) SEQUENCE CHARACTERISTICS:
          ( A ) LENGTH: 10 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:32:

Xaa Leu Glu Lys Leu Leu Glu Xaa Leu Xaa
 1               5                   10

( 2 ) INFORMATION FOR SEQ ID NO:33:

( i ) SEQUENCE CHARACTERISTICS:
          ( A ) LENGTH: 10 amino acids
          ( B ) TYPE: amino acid
          ( D ) TOPOLOGY: linear (i i) MOLECULE TYPE: peptide (x i) SEQUENCE DESCRIPTION: SEQ ID NO:33:

Xaa Leu Glu Lys Leu Leu Glu Xaa Leu Xaa
1               5                   10

(2) INFORMATION FOR SEQ ID NO:34:

(i) SEQUENCE CHARACTERISTICS:
      (A) LENGTH: 10 amino acids
      (B) TYPE: amino acid
      (D) TOPOLOGY: linear (i i) MOLECULE TYPE: peptide (x i) SEQUENCE DESCRIPTION: SEQ ID NO:34:

Xaa Leu Glu Lys Leu Leu Glu Xaa Leu Xaa
1               5                   10

(2) INFORMATION FOR SEQ ID NO:35:

(i) SEQUENCE CHARACTERISTICS:
      (A) LENGTH: 10 amino acids
      (B) TYPE: amino acid
      (D) TOPOLOGY: linear (i i) MOLECULE TYPE: peptide (x i) SEQUENCE DESCRIPTION: SEQ ID NO:35:

Xaa Leu Glu Lys Leu Leu Glu Xaa Leu Xaa
1               5                   10

(2) INFORMATION FOR SEQ ID NO:36:

(i) SEQUENCE CHARACTERISTICS:
      (A) LENGTH: 10 amino acids
      (B) TYPE: amino acid
      (D) TOPOLOGY: linear (i i) MOLECULE TYPE: peptide (x i) SEQUENCE DESCRIPTION: SEQ ID NO:36:

Xaa Leu Glu Lys Leu Leu Glu Xaa Leu Xaa
1               5                   10

(2) INFORMATION FOR SEQ ID NO:37:

(i) SEQUENCE CHARACTERISTICS:
      (A) LENGTH: 10 amino acids
      (B) TYPE: amino acid
      (D) TOPOLOGY: linear (i i) MOLECULE TYPE: peptide (x i) SEQUENCE DESCRIPTION: SEQ ID NO:37:

Xaa Leu Glu Lys Leu Leu Glu Xaa Leu Xaa
1               5                   10

SYNTHETIC LUNG SURFACTANT HAVING ANTIOXIDANT PROPERTIES

CROSS-REFERENCE TO RELATED APPLICATION

This is a continuation of application Ser. No. 08/245,506, filed May 17, 1994 now abandoned, which is a continuation of application Ser. No. 08/049,014 filed Apr. 16, 1993 now abandoned which is a divisional of application Ser. No. 07/789,918 filed Nov. 4, 1991 now U.S. Pat. No. 5,272,252 issued Dec. 21, 1993 which is herein incorporated by reference.

FIELD OF THE INVENTION

This invention relates to the synthesis of a series of polypeptides having antioxidant properties useful as synthetic lung surfactants, the preparation of mixtures of these polypeptides with lipids, the method for production of same and pharmaceutical compositions which are effective in the treatment of mammalian respiratory distress syndrome.

BACKGROUND OF THE INVENTION

The lungs exist in a delicate balance between toxic oxidants and the protective activities of antioxidant defense systems. An imbalance in this system, either through an increase in oxidants or a dysfunction of the protective antioxidant defense systems, can lead to pathophysiological events in the lung causing pulmonary dysfunction. One type of pulmonary dysfunction in which an increase in oxidants can contribute is respiratory distress syndrome (RDS).

Infantile respiratory distress syndrome is a leading cause of death in the first 28 days of life. It strikes 1 in 100 babies worldwide and about 10 percent die. The syndrome rarely occurs in term infants but is generally associated with immaturity and low-birth weight (under 2 kg). Adult RDS shows similar clinical characteristics and pathophysiology to the infantile disease and is managed in the intensive care facility in a similar fashion. The adult disease has diverse etiologies and results from lung insults such as diffuse infections, aspiration of the gastric contents, inhalation of irritants and toxins, and pulmonary edema arising from such sources as narcotic overdose.

RDS is correlated with an absence or dysfunction of the lung surfactant which coats the alveoli of the lungs where gas exchange occurs, and has been associated with oxygen centered free radicals known as oxidants such as superoxide radicals, hydroxyl radicals, hydrogen peroxide which can generate hydroxyl radicals, and lipid peroxides, which have been implicated in cellular injury (Heffner, et al., *Am Rev. Respir. Dis.*104:531–554 1989); (Halliwell, FASEB J. 1:358–364 1987).

The synthetic lung surfactant polypeptides of the present invention, without the antioxidant moieties, have been described in U.S. patent application Ser. Nos. 282,795 filed Dec. 9, 1988 and Ser. No. 214,228 filed Jul. 1, 1988 which are incorporated herein by reference. However, it is an object of the present invention to provide an effective synthetic lung surfactant having antioxidant properties, i.e., the ability to inhibit oxidation of susceptible compounds into oxidants.

Some synthetic lung surfactant preparations have added therapeutic agents such as Vitamin E to surfactant preparations as a separate component (U.S. Pat. No. 4,765,987; PCT publication no. WO 90/11768; PCT publication no. WO 90/07469). However, in the present invention the antioxidants are not a separate component but are actually incorporated into a polypeptide. An advantage of incorporating the antioxidant into the polypeptide is that instead of having a three component mixture (lipid, polypeptide and antioxidant), a two component mixture is available. This can be a significant advantage in testing for efficacy for a marketable pharmaceutical where a variety of dosages and formulations must be tested for each component. Additionally, a two component formulation is easier to manufacture.

The polypeptides of the present invention may be used singly in mixtures with lipid or in combination in mixtures of lipid wherein the polypeptide comprises a minor component of the surfactant mixture. The composition of the present invention may be prepared in high purity and in a standardized fashion as it is a defined mixture of synthetic components. Also, the components are not derived from animal sources which minimizes the risk of contamination by viruses and bacteria.

SUMMARY OF THE INVENTION

The present invention comprises synthetic lung surfactant consisting of a complex of a polypeptide and lipids wherein the polypeptide has the following formula:

optically active isomer or pharmaceutically acceptable salt thereof, wherein:

X is hydrogen, a $C_{1-5}$ alkyl group, a $C_{1-10}$ acyl group, an amino acid, dipeptide or tripeptide;

Y and Y' are each independently a bond, -(Set)n- where n is an integer of from 1 to 3, or T, wherein T is:

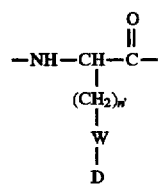

n' is an integer from 1–8; W is —NHC(O)—, —NHCH$_2$—, —OC(O)—, —C(O)O—, —SC(O)—, or —SS—; and D is:

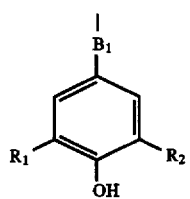

Da or

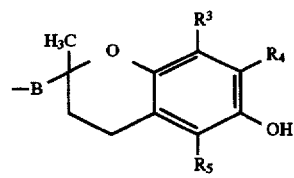

Db wherein B is a bond, $C_{1-16}$ alkylene, or $C_{2-16}$ alkenylene, and $B_1$ is B or

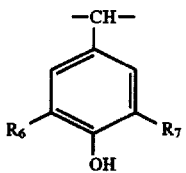

wherein each $R_1$, $R_2$, $R_3$, $R_4$, $R_5$, $R_6$ and $R_7$ is independently a $C_{1-6}$ alkyl;

or X and Y together are Da-C(O)— or Db-C(O)—;

Q is hydroxy, amino, alkylamino, alkoxy group, —O-Da, or —O-Db;

Z is a peptide residue of from 8 to 25 amino acid residues consisting of a fragment of the oligomer having the sequence

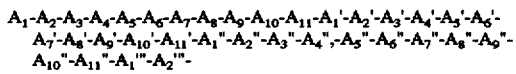

and which may begin with any one of the amino acids residues designated $A_1$–$A_{12}$
wherein $A_1$, $A_1'$, $A_1''$, $A_1'''$, $A_4$, $A_4'$, $A_4''$, $A_8$, $A_8'$, and $A_8''$ are each independently selected from the group of hydrophilic amino acid residues consisting of -Glu-, -Asp-, -Ala-, -Gln-, -Asn-, -Gly-, -Ser-, -Thr-, -Lys-, -Arg-, -Orn-, and -hArg-;

$A_2$, $A_2'$, $A_2''$, $A_2'''$, $A_3$, $A_3'$, $A_3''$, $A_6$, $A_6'$, $A_6''$, $A_7$, $A_7'$, $A_7''$, $A_{10}$, $A_{10}'$, and $A_{10}''$ are each independently selected from the group of lipophilic amino acid residues consisting of -Leu-, -Nle-, -Met-, -Ala-, -Val-, -Phe-, -Nva-, -Ile-, and -Tyr-, or amino acid derivative residue T;

$A_5$, $A_5'$, $A_5''$, $A_{11}$, $A_{11}'$, and $A_{11}''$ are each independently selected from the group of basic amino acid residues consisting of -Lys-, -Orn-, -Arg-, or -hArg-;

Ag, Ag', Ag" are each independently selected from the group of lipophilic, neutral or basic amino acid residues consisting of -Leu-, -Nle-, -Met-, -Ala-, -Val-, -Phe-, -Nva-, -Ile-, -Tyr-, -Thr-, -Ser-, -Gln-, -Asn-, -Gly-, -Lys-, -Arg-, -hArg-, -Trp-, -Orn-, -Trp(For)-, or amino acid derivative residue T;

with the proviso that there is at least one T, —O-Da, O-Db, Da-C(O)— or Db-C(O)— in Formula 1.

The lipid is comprised of one or more of the type associated with natural pulmonary surfactant.

These polypeptide-lipid complexes and their pharmaceutical compositions are useful in treating mammalian respiratory distress syndrome.

DETAILED DESCRIPTION OF THE INVENTION

Figure 1:
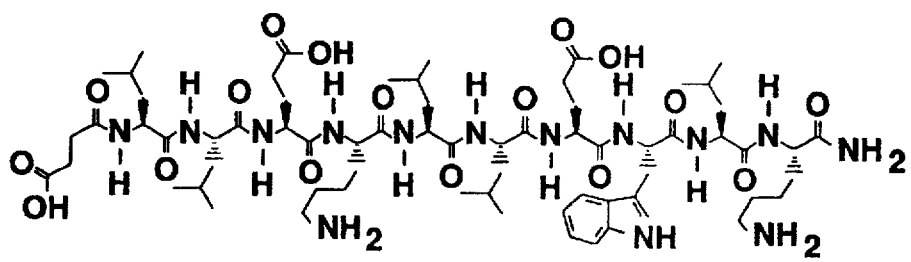
FIG. 1 shows structures of WMAP10 and derivative antioxidant peptides of the present invention.
Figure 1:
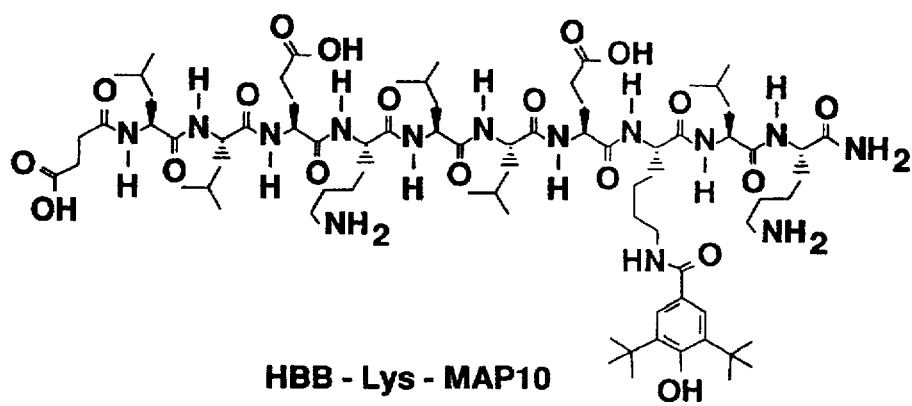
Figure 1:
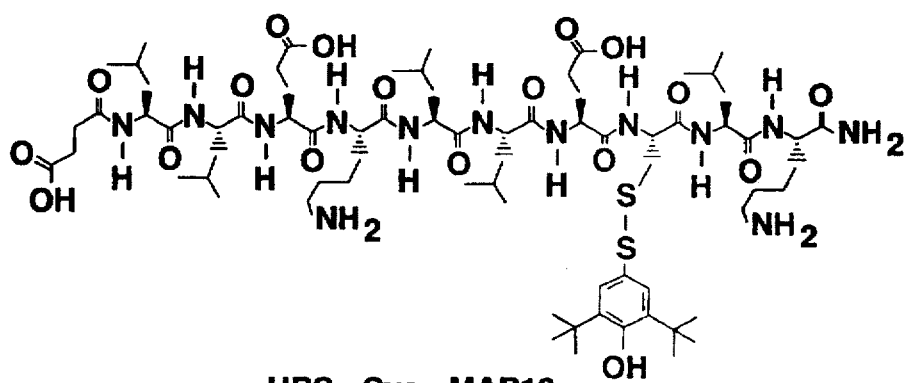
Figure 1:
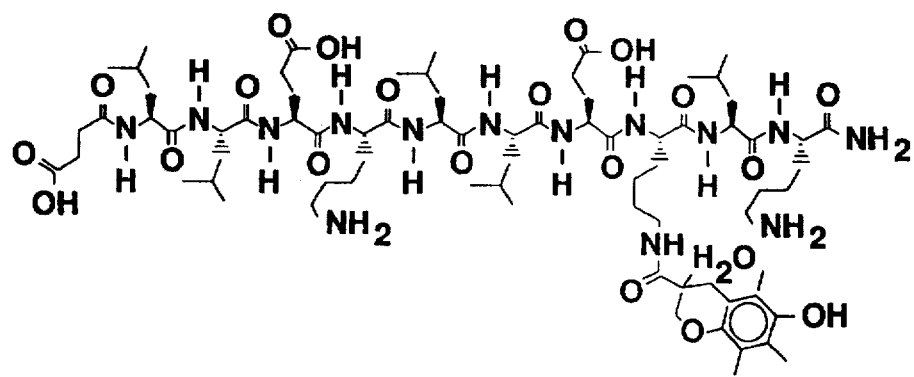
Figure 2A:
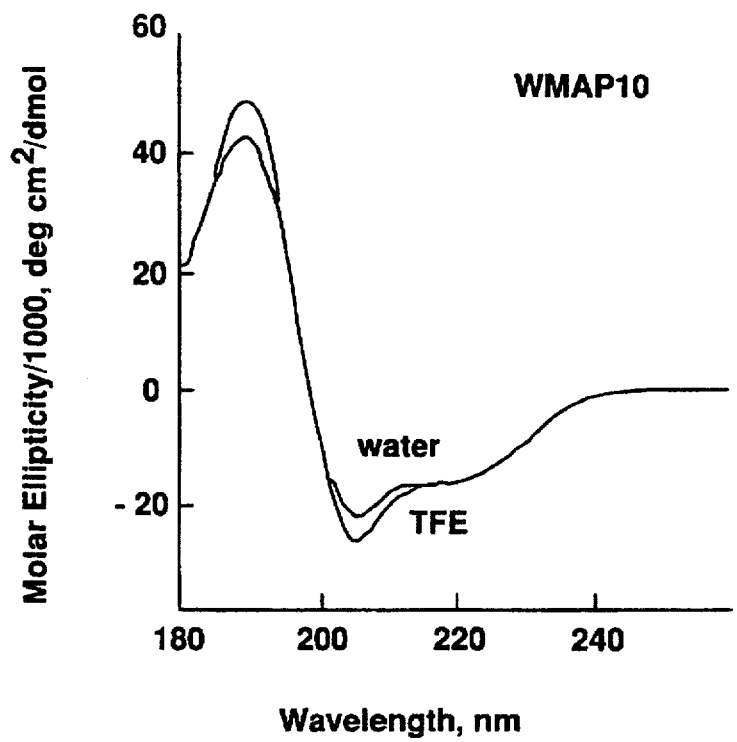
FIG. 2 shows CD spectra of peptides and antioxidant peptides in trifluoroethanol (TFE) and water.
Figure 2B:
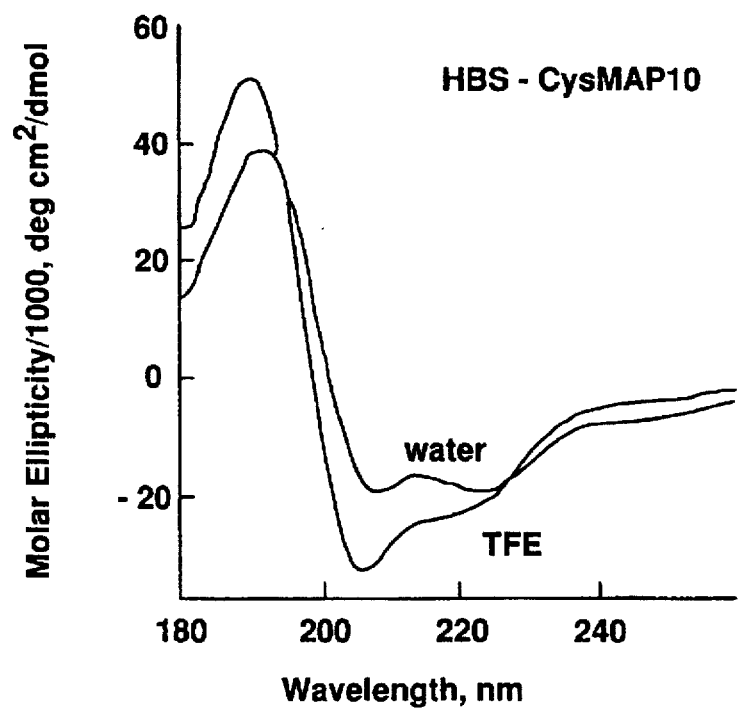
Figure 2C:
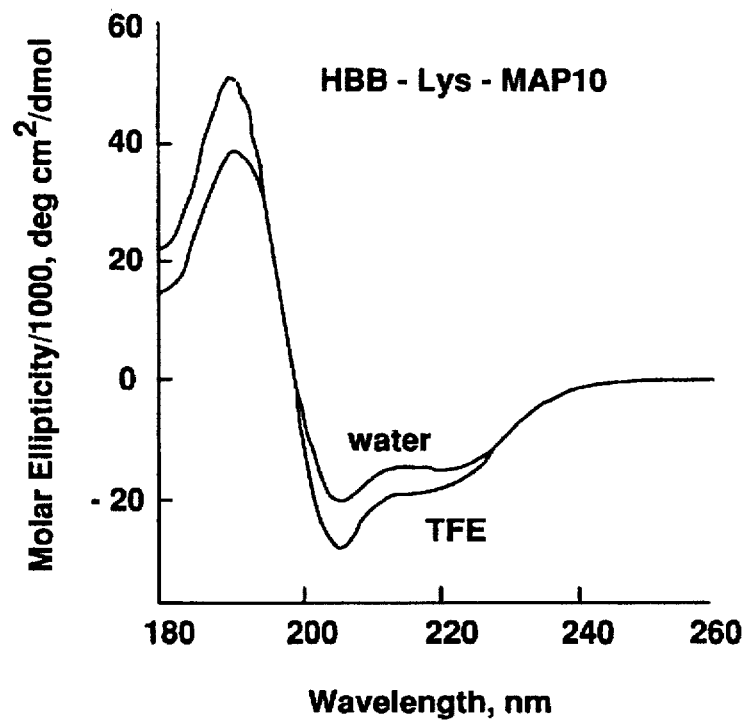
Figure 2D:
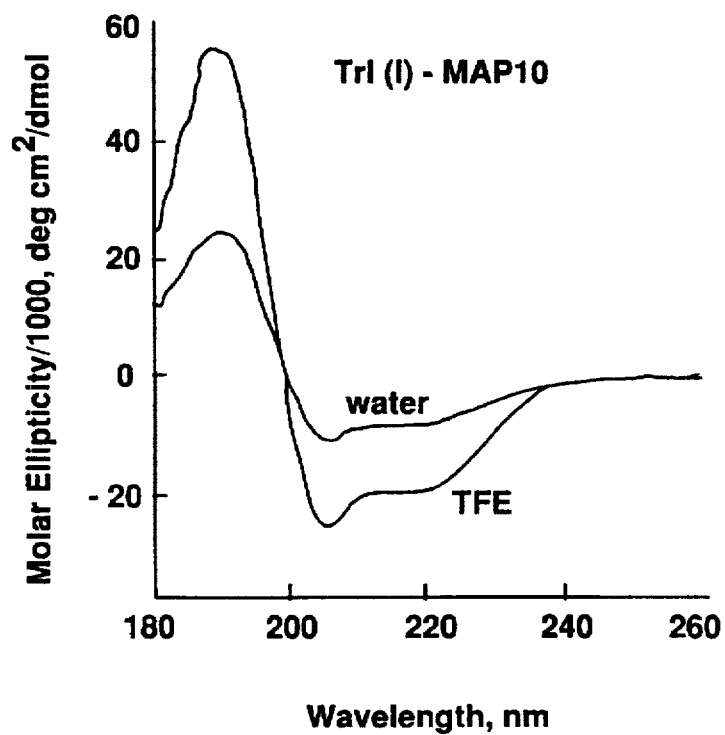

The following common abbreviations of the naturally occurring amino acids are used throughout this specification:

Ala or A - alanine  
Val or V - valine  
Leu or L - leucine  
Ile or I - isoleucine  
Phe or F - phenylalanine  
Trp or W - tryptophan  
Met or M - methionine  
Ser or S - serine  
Tyr or Y - tyrosine  
Asp or D - aspartic acid  
Glu or E - glutamic acid  
Gln or Q - glutamine  
Thr or T - threonine  
Gly or G - glyycine  
Lys or K - lysine  
Arg or R - arginine  
Asn or N - asparagine  
Nle - norleucine  
Orn - ornithine  
hArg - homoarginine  
Nva - norvaline  
Trp(For) - N-formyl-Trp The natural amino acids, with the exception of glycine, contain a chiral carbon atom. Unless otherwise specifically indicated, the optically active amino acids, referred to herein, are of the L-configuration. Preferably, all of the amino acids in the polypeptide are either all D configuration or all L configuration. Once the antioxidant moiety of the present invention is added to the peptide, stereoisomers can be formed. The present invention comprises mixtures of such stereoisomers as well as the isolated stereoisomer. As is customary, the structure of peptides written out herein is such that the amino terminal end is on the left side of the chain and the carboxy terminal end is on the right side of the chain.

When two or more amino acids combine to form a peptide, the elements of water are removed, and what remains of each amino acid is called a residue. "Residue" is therefore an amino acid that lacks a hydrogen atom of the terminal amino group, and/or lacks the hydroxyl group of the terminal carboxyl group. Using accepted terminology, a dash (-) in front of (indicating loss of a hydrogen) and/or after (indicating loss of the hydroxyl) a three letter code for an amino acid or amino acid derivative indicates a residue.

"Alkyl" as used herein means a straight or branched chain hydrocarbon radical such as methyl, ethyl, propyl, butyl, isopropyl, tert-butyl, sec-butyl, isopentyl, 1-methylbutyl and so on, depending upon the number of carbon atoms specified. "Acyl" as used herein means a radical formed from an organic acid by removal of a hydroxyl group; the general formula is RCO— where R may be aliphatic, alicyclic, aromatic hydrocarbon or hydrogen (formyl group). The R group may be substituted. An example of an acyl group is succinyl.

The X group of the present invention may be a hydrogen, a $C_{1-5}$ alkyl group, a $C_{1-10}$ acyl group, an amino acid, dipeptide or tripeptide. Any amino acid, dipeptide or tripeptide can be X which does not interfere with the function of the polypeptide as described herein. The amino acid, dipeptide or tripeptide can be attached to Y, or to Z when Y is a bond, by any suitable method such as solid phase sequential procedure, described hereafter. When X is a $C_{1-5}$ alkyl group, the alkyl group can be added to Y, or to Z when Y is a bond, by any appropriate alkylating method. When X is a $C_{1-10}$ acyl group, the acyl group can be added to Y, or Z when Y is a bond, by any appropriate acylating method.

Both Y and Y' are each independently either a bond, one to three Serine residues or derivatized amino acid T. When Y or Y' are one to three Serine residues, the Serine residues can be attached to Z by any appropriate method such as solid phase sequential procedure, described hereafter. T can also be attached to the polypeptide Z as a derivatized amino acid by any appropriate method such as solid phase sequential procedure.

T is defined as:

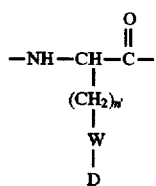

wherein n' is an integer from 1-8, and is preferably an integer from 1 to 4; W is —NHC(O)—, —NHCH$_2$—, —OC(O)—, —C(O)O—, —SC(O)—, or —SS—, and is preferably —NHC(O)— or —SS—; and D is:

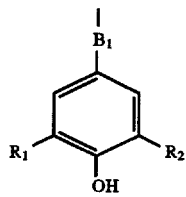  Da wherein B is a bond, $C_{1-16}$ alkylene, or $C_{2-16}$ alkenylene, and $B_1$ is B or

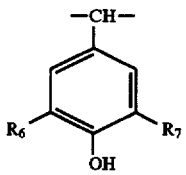

wherein each $R_1$, $R_2$, $R_3$, $R_4$, $R_5$, $R_6$ and $R_7$ is independently a $C_{1-6}$ alkyl. As previously stated, the alkyl can be a straight or branched chain alkyl and each of $R_{1-7}$ can be a different alkyl containing from 1 to 6 carbon atoms. Preferably, $R_1$, $R_2$, $R_6$ and $R_7$ are each tert-butyl, and each of $R_3$, $R_4$ and $R_5$

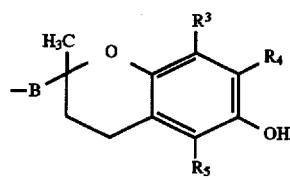 Db are methyl. Da is preferable to Db, and B is preferable to $B_1$. B is preferably a bond.

D is referred to herein as "antioxidant moiety" because it is believed that D is that portion which confers antioxidant properties on the polypeptide. However, it is to be understood that D requires linkers to the polypeptide so that when "antioxidant moieties attached to the polypeptide" are described, it also includes the appropriate likers, e.g., W, —C(O)— or —O—.

One way in which to form T is to modify the side chain of an amino acid receptive to attachment of an antioxidant compound. Amino acids receptive to this attachment typically have a functional group on the side chain thereof. Some examples of these amino acids are amino acids with amino side chain ($N^\varepsilon$) functional groups such as Lysine and Ornithine; amino acids with hydroxy side chain functional groups such as Serine and Threonine; amino acids with sulfhydryl side chain functional groups such as Cysteine and Homocysteine; and amino acids with carboxyl side chain functional groups such as Aspartic acid and Glutamic acid. Amino acid derivatives with side chain functional groups may also be used and many are commercially available.

There are many ways to form T. For example, the side chain amino group, the side chain alcohol group or the side chain sulfhydryl group of an amino acid or amino acid derivative can be acylated by an acylating agent formed from antioxidant compounds. To be an acylating agent, the antioxidant compounds can, for example, form a symmetrical anhydride or an active ester, e.g., N-hydroxybenzotriazole ester (HOBt ester). The acylating agent is then exposed to the unprotected functional target site for the reaction to take place. This is preferably performed in solid phase peptide synthesis while the amino acid to receive the antioxidant moiety is part of the peptide attached to the resin.

Individual amino acids can also be modified prior to incorporation into the peptide by, for example, esterification, reductive alkylation, etc. Other modifications of amino acids and amino acid derivatives containing functional groups are well known in the art.

Preferred examples of antioxidant compounds found to be useful in reacting with amino acids or amino acid derivatives in the present invention are as follows:

1) HBB 3,5-di-t-butyl-4-hydroxybenzoic acid
2) HBP 3-(3',5'-di-tert-butyl-4-hydroxyphenyl)-propionic acid
3) 3,5-di-tert-butyl-4-hydroxycinnamic acid
4) HBA 2-(3',5'-di-t-butyl-4-hydroxyphenyl) acetic acid
5) di-HBA 2,2-di-(3',5'-di-t-butyl-4-hydroxyphenyl)-acetic acid
6) Trl 6-hydroxy-2,5,7,8-tetramethylchroman-2-carboxylic acid—also known as Trolox
7) HBB-al 3,5-di-t-butyl-4-hydoxybenzaldehyde
8) HBB-ol 3,5-di-t-butyl-4-hydroxybenzyl alcohol
9) HBS 3,5-di-t-butyl-4-hydroxythiophenol Preferably HBS, HBB, HBP, HBA, di-HBA and Trl are used when the functional group is a sulfhydryl group, and HBB, HBP, HBC, HBA, di-HBA, and Trl preferably are used when the functional group is either an alcohol group or an amino group. HBB-al can be used for reductive alkylation of amine side chains, and HBB-ol can be used for esterification of acidic side chains and the carboxylic terminus.

The foregoing antioxidant compounds are commercially available or the synthesis known in the art, e.g., 3,5-di-t-butyl-4-hydroxyphenylacetic acid is described in Izv. Akad. Nauk SSSR, Sen Khim., 358 1965 and 3,5-di-t-butyl-4-hydroxy-benzaldehyde is described in J. Org. Chem., 22, 1333 1957. Generally, any antioxidant compound may be used in the present invention which (1) can be attached to the polypeptide of the present invention, (2) exhibits antioxidant activity while attached to the polypeptide, and (3) permits the polypeptide to perform as described herein.

As previously described, when the antioxidant compound and the amino acid or amino acid derivative as described herein react, an amino acid derivative is formed, the residue of which is represented by T in Formula 1. Examples of abbreviations for T and other groups used herein follow:

-[Nε-HBB-Lys]- which means:

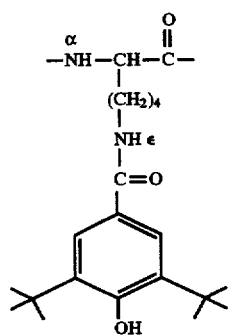

Note that Nε means the side chain amino group to which HBB (without the hydroxyl group due to the reaction) is attached;

-[S-HBS-Cys]- which means HBS (without the hydrogen of the sulfhydryl group) attached to the side chain of the Cysteine residue at the sulfur radical:

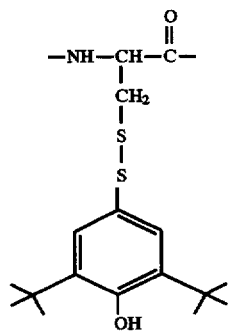

-[O-HBB-Ser]- which means HBB (without the hydroxyl group) attached to the oxygen on the side chain of a Serine residue:

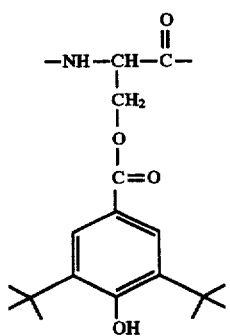

HBC-Leu—which means HBC (without the hydroxyl group) attached to the α-amino group of a Leucine residue:

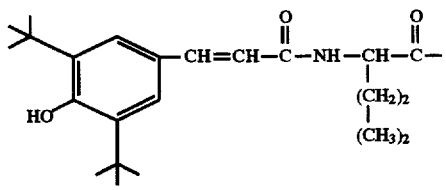

Nα-Fmoc-Nε-Boc-Lys[Nε-HBB-al] which means a Lysine amino acid wherein the Nα is protected by Fmoc, the Nε is protected by Boc and HBB-al (without the oxygen atom) is attached to the $N^ε$ position:

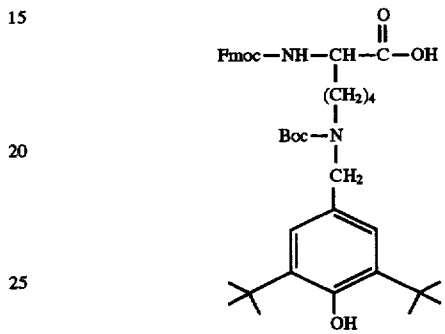

Fmoc-Glu[λ-HBB ester] means a glutamic acid amino acid with the Nα protected by Fmoc, and HBB-ol (without the hydroxyl group) attached to the side chain carboxyl group of glutamic acid to form an ester:

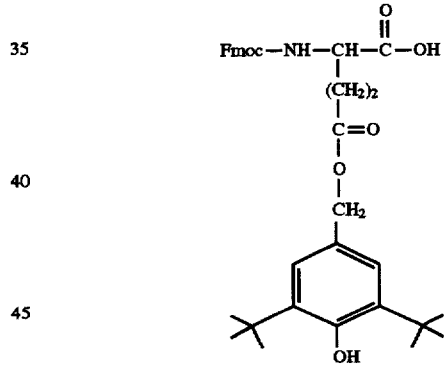

Trl-Leu—which means trolox (without the hydroxyl group) attached to the α-amino group of a Leucine residue:

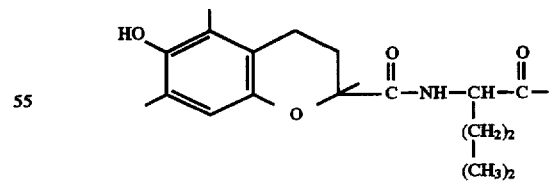

As shown by the Trl-Leu example, the antioxidant moiety, in this case where D=Db and B=a bond, together with a carbonyl group (C(O)—) can be attached to the α-amino terminus of polypeptide Z, i.e., X and Y together form Db-C(O)—. Additionally, the antioxidant moiety Da or Db can attach to the carboxy terminus (—COOH) to form the terminus —C(O)—O-Da or —C(O)—O-Db, i.e., Q=—O-Da or —O-Db. The antioxidant compound can form an acylating agent as previously described and be coupled to each of the termini.

The antioxidant moiety can be attached to side chains between the termini of the polypeptide Z by modifying amino acids to form T, or on at least one terminus. When the antioxidant moiety is attached to a side chain between the termini, it is preferably attached to a portion of the peptide which is lipophilic such as $A_2, A_2', A_2'', A_2''', A_3, A_3', A_3'', A_6, A_6', A_6'', A_7, A_7', A_7'', A_9, A_9', A_9'', A_{10}, A_{10}',$ or $A_{10}''$ in order to maintain the conformation of the peptide. There can be one or more antioxidant moieties attached to the polypeptide Z.

The polypeptides of this invention can be prepared by a variety of procedures readily known to those skilled in the art such as solution phase chemistry. A preferred method is the solid phase sequential procedure which can use automated methods such as the ABI peptide synthesizer. In solid phase sequential procedure, the following steps occur: (1) a first amino acid, having a protected α-amino group, is bound to a resin support; (2) the carboxylic group of a second amino acid, having a protected α-amino group, is activated; (3) the first amino acid is deprotected with a reagent which permits the first amino acid to remain attached to the resin; and (4) coupling occurs between the α-amino group of the first amino acid and the activated carboxylic group of the second amino acid. These steps are repeated with new amino acid residues which permits the formation of the peptide. When the desired length of peptide has been formed, the peptide is cleaved from the resin, deprotected and recovered.

The resin support employed can be any suitable resin conventionally employed in the art for the solid phase preparation of polypeptides such as a polystyrene which has been cross-linked with from 0.5 to about 3 percent divinyl benzene, which has been either chloromethylated or hydroxymethylated to provide sites for ester formation with the initially introduced α-amino protected amino acid. Other suitable resin supports are pMHBA (Peptide International, Louisville, Ky.), RINK (Calbiochem, LaJolla, Calif.) and Sasrin (Biochem, Philadelphia, Pa.). The Sasrin resin requires a special ABI cycle for loading the first amino acid which is described in the ABI peptide sysnthesizer user's manual. The first amino acid, having a protected α-amino group, is attached to the resin as described in the Applied Biosystems Model 430A Peptide Synthesizer User's Manual, incorporated in its entirety herein.

Preferred methods of activating the second amino acid include formation of a symmetrical anhydride or active ester of the second α-amino protected amino acid. For example, an α-amino protected amino acid can be reacted with dicyclohexylcarbodiimide (DCC) in the presence of dichloromethane (DCM) to form the symmetrical anhydride. Alternatively, a HOBt active ester can be formed by dissolving Boc-amino acid (tert-butyloxycarbonyl-amino acid) and HOBt in DCC and chilling, adding additional DCC and warming the solution to room temperature. This solution is then added to the amino acid bound resin. This method of activation to form acylating agents may also be used for the antioxidant compounds.

If there are other functional groups present besides the α-amino group, those groups will also have to be protected. Generally, the α-amino group and each of the side chain functional groups can be protected by different protecting groups so that one protecting group can be removed without removing the other protecting groups.

Among the classes of α-amino protecting groups contemplated for use with the present invention are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and γ-chlorobutyryl; (2) aromatic urethan type protecting groups such as benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 1-(p-biphenyl)-1-methylethoxycarbonyl, α,α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl or 9-fluorenylmethoxycarbonyl (Fmoc); (6) alkyl type protecting groups such as triphenylmethyl (trityl) and benzyl; (7) trialkylsilane groups such as trimethylsilane.

The selection of the α-amino protecting group, however, will depend upon the resin used, the target site functional group, the other functional groups present in the polypeptide and whether the amino acid derivative T can withstand cleavage from the resin with the cleavage reagent. For example, to prepare Suc-Leu-Leu-Glu-Lys-Leu-Leu-Glu-$N^\varepsilon$-HBB-Lys-Leu-Lys-$NH_2$, (SEQ ID NO. 1:), a pMBHA resin is used, which produces a C terminal amino group. The α-amino protecting group is Boc, the target site side chain amino (Ns) protecting group is Fmoc, the non-target site Nε protecting group is 2ClZ (2-Chlorobenzyloxycarbonyl), the non-target site COOH protecting group is OBzl (Benzyl ester) and the peptide is constructed using standard t-Boc chemistry on an ABI430A peptide synthesizer. The $N^\varepsilon$-Fmoc can be selectively removed with piperidine, and HBB introduced as an HOBT active ester in order to attach EBB at the target site Lysine side chain. Anhydrous hydrofluoric acid (HF) can be used to simultaneously cleave the peptide from the resin and to remove the remaining protecting groups.

The selection of appropriate combination of protecting groups and reagents to selectively remove protecting groups is well known in the art. For example, see M. Bodanszky, PEPTIDE CHEMISTRY, A PRACTICAL TEXTBOOK, Springer-Verlag (1988); J. Stewart, et al., SOLID PHASE PEPTIDE SYNTHESIS, 2nd ed., Pierce Chemical Co. (1984).

Each protected amino acid or amino acid sequence is introduced into the solid phase reactor in about a four-fold excess and the coupling is carried out in the presence of a coupling agent such as in a medium of dimethylformamide: methylene chloride (1:1) or in dimethylformamide alone or methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser, et al., *Analyt. Biochem.* 34, 595 (1970).

After the desired amino acid sequence has been obtained, the peptide is removed from the resin using any appropriate reagent which will not adversely effect the polypeptide. For example, anyhdrous HF containing 5% anisole and 5% acetonitrile in 0.1% trifluoroacetic acid can be used to cleave the polypeptide from a pMBHA resin.

The polypeptides of Formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower) alkylpiperidine, and any other suitable amine.

The phospholipids of the protein-phospholipid complexes of this invention can be any phospholipid and this term as used herein includes the phosphoglycerides and the sphingolipids. Phosphoglycerides are those di-fatty acid esters of glycerol in which the remaining hydroxy group, a terminal hydroxy group, of the gylcerol moiety forms an ester with phosphoric acid. Commonly the phosphoric acid moiety of the phosphoglycerides forms a second ester with an alcohol such as ethanolamine, serine, choline, or glycerol. Sphingolipids are those mono-fatty acid esters of sphingosine or dihydrosphingosine in which the hydroxy group at the 1-position forms an ester with the choline ester of phosphoric acid. The preferred lipids of the protein-phospholipid complexes of this invention comprise dipalmitoylphosphatidylcholine (DPPC), phosphatidylcholine molecules containing acyl chains of other lengths and degrees of saturation (PC), cardiolipin (CL), phosphatidylglycerols (PG), phosphatidylserines (PS), fatty acids (FA), and triacylglycerols (TG). DPPC comprises the major component of the lung surfactant mixture while PC, CL, PG, PS, FA, and TG comprise minor components. Suitable fatty acids for use in the phospholipids of this invention are long chain carboxylic acids (generally having eight or more carbon atoms), typically unbranched. The fatty acids can be either saturated or unsaturated. Representative fatty acids are lauric, myristic, palmitic, and oleic acids.

Pharmaceutical preparations of the polypeptide or the protein-phospholipid complexes of this invention can be prepared as a dry mixture or in an aqueous suspension, in some instances containing small amounts of organic solvents, such as, for example, ethanol or trifluoroethanol, detergents, such as, for example, sodium dodecyl sulfate or sodium deoxycholate, salts, such as calcium chloride or sodium chloride, carbohydrates, such as glucose, dextrose or mannitol, and amino acids, such as glycine and alanine. Where the pharmaceutical composition is made into liquid form, stabilizers, preservatives, osmotic pressure regulators, buffering agents, and suspending agents of the liquid may be added. If desired, suitable germicides may also be added. The pH of the aqueous suspension may vary between 2 and 10 and may be adjusted with acids and bases, such as, for example, hydrochloric acid, sodium phosphate, or sodium hydroxide. The dry mixture may be reconstituted in an aqueous solution containing pharmaceutically acceptable salts, organic solvents, and detergents. The aqueous preparation may be dialyzed, filtered, or chromatographed to exchange the suspending medium with a pharmaceutically acceptable medium prior to use. The preparation may be administered as a dry powder, an aqueous suspension, or as an aerosol directly into the lungs of the distressed subject. The pharmaceutical composition of the present invention may be charged in hermetically sealed containers such as vials and ampules and be preserved sterilely. The composition may be stored in a vial or ampule separately from a vial or ampule containing the suspension buffer and the dry or hydrated composition may be mixed with the suspension buffer prior to use.

Lipid constitutes from 50 to 99.9% of the lung surfactant preparation. Suitable lipids include DPPC, PC, CL, PG, PS, FA, and TG. DPPC comprises the major lipid species and is present in concentrations of 60 to 100% of the total lipid weight. The remaining lipids are present in minor concentrations. PC, CL, PG and PS may comprise up to 30% of the lipids, and FA and TG may comprise up to 10% of the lipid weight. The fatty acyl chains of the minor lipid components may be saturated or unsaturated and of any chain length. Chain lengths of 12 to 16 carbon atoms and up to 2 unsaturated bonds are preferred. The preferred lipid composition is 85–100% DPPC plus 0–15% of PG.

The lipid components of the synthetic lung surfactant are commonly found in mammalian lung surfactant and are available from common industrial sources in high purity. The polypeptide components are prepared by solid-phase peptide synthesis by methods familiar to those skilled in the art. Mixtures of the lipids of the invention with proteins isolated from mammalian lung lavage have been shown to be effective in treating neonatal RDS. However, mixtures of these lipids with synthetic peptides in lung surfactant preparations have not been reported.

Lipids are mixed in a volatile organic solvent or mixtures of solvents, such as mixtures of chloroform and methanol or trifluoroethanol. The organic solvent is removed by evaporation under nitrogen, argon, or under vacuum. An aqueous solution which may contain organic and inorganic acids, bases, and salts, and saccharides such as dextrose is added to the dry lipid mixture to attain a final concentration of 0.1 to 100 mg of DPPC per ml. In general, it is preferable, but not necessary to warm the mixture to 35°–50° C., mix vigorously, and incubate for up to 2 hours at 25°–50° C. Then, peptide or a mixture of peptides is added as a dry powder or suspended in an aqueous solution in some cases containing a suitable organic solvent, such as ethanol or trifluorethanol, or a denaturing agent, such as guanidinium hydrochloride or urea, which improves the solubility of the peptide in the aqueous suspension. Association of peptide and lipid may be promoted at a particular pH, thus the pH of the aqueous solution may vary from 2 to 10. The preferred method for mixing peptide and lipid is to add dry peptide to lipid in water at 45°–50° C. and to mix by bath ultrasonication at 45°–50° C. for 30–90 minutes, then freeze-dry and store at −20° C.

Lipids are mixed with a suitable detergent such as octylglucoside or sodium deoxycholate at a weight ratio of from 1 to 20 parts of detergent per part of DPPC in water, an aqueous buffer, or saline solution at concentrations from 1 to 100 mg DPPC/ml. Then, peptide is added as a dry powder or suspended in an aqueous solution with or without an organic solvent, denaturing agent, or detergent. The mixture is then dialyzed, filtered, centrifuged or chromatographed to remove the detergent.

Preferably, lipids and peptides are mixed in a volatile organic solvent with or without a small amount of water. The volatile solvent is evaporated under a stream of nitrogen or argon, in a vacuum oven, or by rotary evaporation either before or after addition of an aqueous solvent.

The mixture of lipid and peptide prepared by one of the methods described above is incubated for up to 2 hours, preferably at 35°–50° C. with sonic irradiation. The mixture may then be dialyzed, filtered, or chromatographed to replace the aqueous medium with a pharmaceutically acceptable medium, although this is not necessary. In some cases, efficacy is improved by separating unreacted lipid or peptide from associated lipid and peptide by ultracentrifugation, filtration, or chromatography. The mixture may then be lyophilized or aerosolized.

When the polypeptide-phospholipid complexes of this invention are used in the treatment of neonatal respiratory distress syndrome, a physiological condition which results from the inability of the lungs of premature infants to produce pulmonary surfactant, the complexes act as an antioxidant and synthetic pulmonary surfactants and either replace the natural, missing surfactant or augment the lack of sufficient natural surfactant. Treatment is continued until the infant's lungs produce a sufficient amount of natural, pulmonary surfactant so as to render further treatment unnecessary.

The preparations are preferably those suitable for endotracheal administration, that is as a liquid suspension, a dry powder, or an aerosol. For a liquid suspension, the dry mixture or the mixture in aqueous suspension is mixed with suitable agents, such as water, saline solutions, dextrose, and glycerol to produce a pharmaceutically effective composition. Preferred liquid suspensions will contain 0.8 to 1.0 weight per cent of sodium chloride and will be 1–20 mM, preferably in calcium ion. The preparation is then filter sterilized. In general, the preparation comprises 1 to 100 mg of DPPC per ml and is administered at a dose of 0.2 to 5 ml/kg. To prepare a dry mixture, the aqueous suspension is lyophilized. The aerosol is prepared from a finely divided dry powder suspended in a propellant, such as lower alkanes and fluorinated alkanes, such as Freon. The aerosol is stored in a pressurized container.

For example, the surfactant (polypeptide of the present invention and lipid complex) is administered, as appropriate to the dosage form, by endotracheal tube, by aerosol administration, or by nebulization of the suspension or dry mixture into the inspired gas. The surfactant is administered in one or multiple doses of 10 to 200 mg/kg. The preferred method of administration is as a suspension of peptide and lipid in physiological saline solution at a concentration of 5–10 mg of surfactant per ml through an endotracheal tube, achieving a dose of 50–100 mg/kg.

The polypeptide of the present invention is administered to treat a subject. "Subject" means a mammal, for example, but not limited to, a human being.

The following examples show some methods of preparation for the polypeptide, polypeptide/lipid complex and starting materials of the present invention. The present invention is not limited to the following examples nor to these methods of preparation.

Abbreviations used in the examples not previously defined are as follows:
Standard Boc chemistry and Standard Fmoc chemistry: that chemistry used with the ABI peptide synthesizer respectively for the Boc cycles and the Fmoc cycles.

| TBDMS | Tetrabutyldimethylsilyl |
|---|---|
| SEt | Ethylthio |
| Suc | Succinyl |
| TFA | Trifluoroacetic acid |
| Bzl | Benzyl |
| Ot—Bu | t-butyl ether |

Example 1

1(A). PREPARATION OF POLYPEPTIDE: Suc-Leu-Leu-Glu-Lys-Leu-Leu-Glu-Ne-HBB-Lys-Leu-Lys-NH$_2$ (HBB-Lys-MAP10)_(SEQ ID NO: 2)

Prepare N$^\alpha$-Boc-N$^\epsilon$-Fmoc-Lys-Leu-N$^\epsilon$-2ClZ-Lys-pMBHA Resin using standard t-Boc chemistry on an ABI430A peptide synthesizer (Applied Biosystems Inc., Foster City, Calif.).

Prepare N$^\alpha$-Boc-Lys-Leu-N$^\epsilon$-2ClZ-Lys-pMBHA Resin from N$^\alpha$-Boc-N$^\epsilon$-Fmoc-Lys-Leu-N$^\epsilon$-2ClZ-Lys-pMBHA Resin removing the N$^\epsilon$-Fmoc with piperidine.

Prepare N$^\alpha$-Boc-Lys-Leu-N$^\epsilon$-2ClZ-Lys-pMBHA Resin from N$^\alpha$-Boc-N$^\epsilon$-Fmoc-Lys-Leu-N$^\epsilon$-2ClZ-Lys-pMBHA Resin removing the N$^\epsilon$-Fmoc with piperidine.

Prepare N$^\alpha$-Boc-N$^\epsilon$-HBB-Lys-Leu-N$^\epsilon$-2ClZ-Lys-pMBHA Resin from N$^\alpha$-Boc-Lys-Leu-N$^\epsilon$-2ClZ-Lys-pMBHA Resin and 3,5-di-t-butyl-4-hydroxybenzoic acid as N-hydroxybenzotriazole active ester (2 mmol acid, 4X excess active ester per each of two couplings).

Prepare Leu-Leu-Glu(OBzl)-N$^\epsilon$-2ClZ-Lys-Leu-Leu-Glu(OBzl)-N$^\epsilon$-HBB-Lys-Leu-N$^\epsilon$-2ClZ-Lys-pMBHA Resin (SEQ ID NO: 3) from N$^\alpha$-Boc-N$^\epsilon$-HBB-Lys-Leu-N$^\epsilon$-2ClZ-Lys-pMBHA Resin using standard t-Boc chemistry on an ABI430A peptide synthesizer.

Couple Leu-Leu-Glu(OBzl)-N$^\epsilon$-2ClZ-Lys-Leu-Leu-Glu(OBzl)-N$^\epsilon$-HBB-Lys-Leu-N$^\epsilon$-2ClZ-Lys-pMBHA Resin (SEQ ID NO: 3) with succinic anhydride to give Suc-Leu-Leu-Glu(OBzl)-N$^\epsilon$-2ClZ- Lys-Leu-Leu-Glu(OBzl)-N$^\epsilon$-HBB-Lys-Leu-N$^\epsilon$-2ClZ-Lys-pMBHA Resin (SEQ ID NO: 4).

Cleave Suc-Leu-Leu-Glu(OBzl)-N$^\epsilon$-2ClZ-Lys-Leu-Leu-Glu(OBzl)-N$^\epsilon$-HBB-Lys-Leu-N$^\epsilon$-2ClZ-Lys-pMBHA Resin (SEQ ID NO: 4) from the resin and remove side chain protecting groups in anhydrous HF containing 5% anisole and 5% dimethylsulfide at −5° C. for 1 hour. Extract from resin with 50% acetonitrile in 0.1% trifluoroacetic acid, freeze and lyophilize. Purify by reverse phase HPLC on a Rainin 21.4×250 mm C18 column using a linear 39–46.5% acetonitrile gradient over 15 minutes in 0.1% aqueous trifluoroacetic acid (pH2) at 40 mL/min flow rate monitored by absorbance at 214 nm. Combine pure fractions, freeze and lyophilize to give the title compound. FAB-MS (M+H$^+$) 1558.2

1(B). PREPARATION OF DPPC COMPLEX WITH POLYPEPTIDE DESCRIBED IN EXAMPLE 1(A).

Peptide 1(A) is prepared as described above. DPPC (25 mg) in 1 ml of chloroform is dried under a stream of nitrogen and dried under vacuum to remove traces of organic solvent. To the dry lipid mixture is added 3 ml of water. The preparation is incubated for 1 hour at 45° C. Then, 0.5 mg of dry Peptide i(A) is added to the aqueous preparation. The preparation is sonicated in a bath ultrasonicator at 45° C. for 2 hours. The resulting lipid-peptide mixture is lyophilized and stored at 4° C. for up to one month. Prior to testing, 9 ml of 0.9% NaCl, 20 mM HEPES buffer, pH 7.40 is added. The preparation is incubated for 1 hour at 45° C. with periodic mixing.

EXAMPLE 2

2(A). PREPARATION OF POLYPEPTIDE: Suc-Leu-Leu-Glu-Lys-Leu-Leu-Glu-S-HBS-Cys-Leu-Lys-NH$_2$ (HBS-Cys-MAP10) (SEQ ID NO: 5)

Prepare Leu-Leu-Glu(OBzl)-N$^\epsilon$-2ClZ-Lys-Leu-Leu-Glu(OBzl)-Cys(SEt)-Leu-N$^\epsilon$-2ClZ-Lys-pMBHA (SEQ ID NO: 6) Resin using standard t-Boc chemistry on an ABI430A peptide synthesizer.

Couple Leu-Leu-Glu(OBzl)-N$^\epsilon$-2ClZ-Lys-Leu-Leu-Glu(OBzl)-Cys(SEt)-Leu-N$^\epsilon$-2ClZ-Lys-pMBHA Resin (SEQ ID NO: 6) with succinic anhydride to give Suc-Leu-Leu-Glu(OBzl)-N$^\epsilon$-2ClZ-Lys-Leu-Leu-Glu(OBzl)-Cys(SEt)-Leu-N$^\epsilon$-2ClZ-Lys-pMBHA Resin (SEQ ID NO: 7).

Mix Suc-Leu-Leu-Glu(OBzl)-N$^\varepsilon$-2ClZ-Lys-Leu-Leu-Glu(OBzl)-Cys(SEt)-Leu-N$^\varepsilon$-ZClZ-Lys-pMBHA Resin (SEQ ID NO: 7) (0.263 g), anhydrous dimethylformamide (5 mL) and methyl thioglycolate (450µL). Stir under an argon atmosphere overnight to give Suc-Leu-Leu-Glu(OBzl)-N$^\varepsilon$-2ClZ-Lys-Leu-Leu-Glu(OBzl)-Cys-Leu-N$^\varepsilon$-2ClZ-Lys-pMBHA Resin (SEQ ID NO: 8).

Cleave Suc-Leu-Leu-Glu(OBzl)-N$^\varepsilon$-2ClZ-Lys-Leu-Leu-Glu(OBzl)-Cys-Leu-N$^\varepsilon$-2ClZ-Lys-pMBHA Resin (SEQ ID NO: 8) from the resin and remove side chain protecting groups in anhydrous HF containing 5% anisole and 5% dimethylsulfide at –5° C. for 1 hour. Extract from the resin with 50% acetonitrile in 0.1% trifluoroacetic acid, freeze and lyophilize. Purify by reverse phase HPLC on a Rainin 21.4×250 mm C18 column using a linear 34–44% acetonitrile gradient over 15 minutes in 0.1% aqueous trifluoroacetic acid (pH 2) at 40 mL/minutes flow rate monitored by absorbance at 214 nm. Combine pure fractions, freeze and lyophilize to give Suc-Leu-Leu-Glu-Lys-Leu-Leu-Glu-Cys-Leu-Lys-N$_2$ (SEQ ID NO: 9).

Combine 3,5-di-t-butyl-4-hydroxythiophenol (751 mg), diethylazodicarboxylate (496µL, 3.15 mmol) and p-dioxane (5 mL). Place under an argon atmosphere and stir for 2 hours to give a complex of 3,5-di-t-butyl-4-hydroxythiophenol and diethyl azodicarboxylate.

Treat Suc-Leu-Leu-Glu-Lys-Leu-Leu-Glu-Cys-Leu-Lys-NH$_2$ (SEQ ID NO: 9) (32 mg) with 1.1 equivalents of the preformed complex of 3,5-di-t-butyl-4-hydroxythiophenol and diethyl azodicarboxylate (1.1 equivalents) in p-dioxane (80 µL) and dimethylformamide (40 µL). Place under an argon atmosphere and stir overnight. Pour into 25% acetonitrile in 0.1% trifluoroacetic acid, freeze and lyophilize. Purify by reverse phase HPLC on a Rainin 21.4×250 mm C18 column using a linear 44.5–52% acetonitrile gradient over 15 minutes in 0.1% aqueous trifluoroacetic acid (pH 2) at 41 mL/minutes flow rate monitored by absorbance at 214 nm. Combine pure fractions, freeze and lyophilize to give the title compound. FAB-MS(M+H$^+$) 1536.5.

2(B). PREPARATION OF DPPC COMPLEX OF THE POLYPEPTIDE DESCRIBED IN EXAMPLE 2(A).

Peptide 2(a) is mixed with DPPC as described under Example 1 except that the final suspending buffer contains 5 mM CaCl$_2$ in addition to 0.9% NaCl, 20mM HEPES buffer, pH 7.40.

EXAMPLE 3

3(A). PREPARATION OF POLYPEPTIDE: HBC-Leu-Leu-Glu-Lys-Leu-Leu-Glu-L s-Leu-Lys-NH$_2$ (SEQ ID NO: 10)

Prepare Leu-Leu-Glu(Ot-Bu)-N$^\varepsilon$-Boc-Lys-Leu-Leu-Glu(Ot-Bu)-N$^\varepsilon$-Boc-Lys-Leu-Ns-Boc-Lys-pMBHA Resin (SEQ ID NO: 11) on an ABI430A peptide synthesizer using standard N$^\alpha$-Fmoc protection and HOBT active esters.

Prepare HBC-Leu-Leu-Glu(Ot-Bu)-N$^\varepsilon$-Boc-Lys-Leu-Leu-Glu(Ot-Bu)-N$^\varepsilon$-Boc-Lys-Leu-Ne-Boc-Lys-pMBHA Resin (SEQ ID NO: 12) from Leu-Leu-Glu(Ot-Bu)-N$^\varepsilon$-Boc-Lys-Leu-Leu-Glu(Ot-Bu)-N$^\varepsilon$-Boc-Lys-Leu-N$^\varepsilon$-Boc-Lys-pMBHA Resin (SEQ ID NO: 11) and 3,5-di-t-butyl-4-hydroxycinnamic acid as N-hydroxybenzotriazole active ester (2 mmol acid, 4X excess active ester per each of two couplings).

Cleave HBC-Leu-Leu-Glu(Ot-Bu)-N$^\varepsilon$-Boc-Lys-Leu-Leu-Glu(Ot-Bu)-N$^\varepsilon$-Boc-Lys-Leu-Ns-Boc-Lys-pMBHA Resin (SEQ ID NO: 12) from the resin and remove side chain protecting groups using 50% trifluoroacetic acid in methylene chloride. Place under argon atmosphere and stir for 1 hour. Evaporate the solvent in vacuo and purify by reverse phase HPLC to give the title compound.

EXAMPLE 4

4(A). PREPARATION OF POLYPEPTIDE: Suc-Leu-Leu-Glu-Lys-Leu-Leu-Glu-Lys-Leu-L s 3 5-di-t-butyl-4-hdroxybenzyl ester (SEQ ID NO: 13)

Prepare Leu-Leu-Glu(Ot-Bu)-N$^\varepsilon$-Boc-Lys-Leu-Leu-Glu(Ot-Bu)-N$^\varepsilon$-Boc-Lys-Leu-Ns-Boc-Lys-Sasrin Resin (SEQ ID NO: 14) on an ABI430A peptide synthesizer using standard N$^\alpha$-Fmoc protection and HOBT active esters.

Couple Leu-Leu-Glu(Ot-Bu)-Ne-Boc-Lys-Leu-Leu-Glu(Ot-Bu)-N$^\varepsilon$-Boc-Lys-Leu-Ne-Boc-Lys-Sasrin Resin (SEQ ID NO: 14) with succinic anhydride to give Suc-Leu-Leu-Glu(Ot-Bu)-N$^\varepsilon$-Boc-Lys-Leu-Leu-Glu(Ot-Bu)-N$^\varepsilon$-Boc-Lys-Leu-Ne-Boc-Lys-Sasrin Resin (SEQ ID NO: 15).

Cleave Suc-Leu-Leu-Glu(Ot-Bu)-Ne-Boc-Lys-Leu-Leu-Glu(Ot-Bu)-N$^\varepsilon$-Boc-Lys-Leu-Ne-Boc-Lys-Sasrin Resin (SEQ ID NO: 15) with 1% trifluoroacetic acid in methylene chloride to give Suc-Leu-Leu-Glu(Ot-Bu)-N$^\varepsilon$-Boc-Lys-Leu-Leu-Glu(Ot-Bu)-Ne-Boc-Lys-Leu-N$^\varepsilon$-Boc-Lys (SEQ ID NO: 15).

Dissolve Suc-Leu-Leu-Glu(Ot-Bu)-N$^\varepsilon$-Boc-Lys-Leu-Leu-Glu(Ot-Bu)-N$^\varepsilon$-Boc-Lys-Leu-N$^\varepsilon$-Boc-Lys (SEQ ID NO: 15) in dimethylformamide and treat with dicyclohexylcarbodiimide (1 equivalents) and 3,5-di-t-butyl-4-hydroxybenzyl alcohol (2 equivalents). Place under an argon atmosphere and stir overnight. Dilute with ethyl acetate, wash with cold 1N hydrochloric acid and purify by HPLC to give Suc-Leu-Leu-Glu(Ot-Bu)-N$^\varepsilon$-Boc-Lys-Leu-Leu-Glu(Ot-Bu)-N$^\varepsilon$-Boc-Lys-Leu-N$^\varepsilon$-Boc-Lys, 3,5-di-t-butyl-4-hydroxybenzyl ester (SEQ ID NO: 16).

Treat Suc-Leu-Leu-Glu(Ot-Bu)-Ne-Boc-Lys-Leu-Leu-Glu(Ot-Bu)-N$^\varepsilon$-Boc-Lys-Leu-N$^\varepsilon$-Boc-Lys, 3,5-di-t-butyl-4-hydroxybenzyl ester (SEQ ID NO: 16) with 50% trifluoroacetic acid in methylene chloride. Place under an argon atmosphere and stir for 1 hour. Evaporate the solvent in vacuo and purify by HPLC to give the title compound.

4(B). PREPARATION OF DPPC COMPLEX OF POLYPEPTIDE DESCRIBED IN 4(A).

The DPPC complex of peptide 4(A) is prepared by mixing with DPPC as described under Example 1(B).

EXAMPLE 5

5(A). PREPARTION OF POLYPEPTIDE: Trl-Leu-Leu-Glu-Lys-Leu-Leu-Glu-Lys-Leu-Lys-NH$_2$ (SEQ ID NO: 17)

Prepare Leu-Leu-Glu(OBzl)-N$^\varepsilon$-2ClZ-Lys-Leu-Leu-Glu(OBzl)-N$^\varepsilon$- 2ClZ-Lys-Leu-Ne-2ClZ-Lys-pMBHA Resin (SEQ ID NO: 18) using standard t-Boc chemistry on an ABI430A peptide synthesizer.

Combine 6-hydroxy-2,5,7,8-tetramethylchroman-2-carboxylic acid (Trolox) (27 mg), dimethylformamide (30 µL) and methylene chloride (250 µL). Add dicyclohexylcarbodiimide (200 µL of a 0.5 M solution in methylene chloride) and stir for 5 minutes to give 6-hydroxy-2,5,7,8-tetramethylchroman-2-carboxylic acid (Trolox) symmetrical anhydride.

Prepare Trl-Leu-Leu-Glu(OBzl)-N$^\varepsilon$-2ClZ-Lys-Leu-Leu-Glu(OBzl)-N$^\varepsilon$-2ClZ-Lys-Leu-N$^\varepsilon$-2ClZ-Lys-pMBHA Resin (SEQ ID NO: 19) from Leu-Leu-Glu(OBzl)-N$^\varepsilon$-2ClZ-Lys-Leu-Leu-Glu(OBzl)-N$^\varepsilon$-2ClZ-Lys-Leu-N$^\varepsilon$-2ClZ-Lys-pMBHA Resin (SEQ ID NO: 18) and 6-hydroxy-2,5,7,8-tetramethylchroman-2-carboxylic acid (Trolox) symmetrical anhydride (2 mmol acid, 10× excess symmetrical anhydride per each of two couplings).

Cleave Trl-Leu-Leu-Glu(OBzl)-Ne-2ClZ-Lys-Leu-Leu-Glu(OBzl)-N$^\varepsilon$-2ClZ-Lys-Leu-Ne-2ClZ-Lys-pMBHA Resin (SEQ ID NO: 19) from the resin and remove side chain protecting groups in anhydrous HF containing 5% anisole and 5% dimethylsulfide at −5° C. for 1 hour. Extract from the resin with 50% acetonitrile in 0.1% trifluoroacetic acid, freeze and lyophilize. Purify by reverse phase HPLC to give the title compound.

5(B). PREPARATION OF DPPC COMPLEX OF POLYPEPTIDE DESCRIBED IN 5(A).

Peptide 5(A) is mixed with DPPC as described in Example 1(B).

EXAMPLE 6

6(A). PREPARATION OF POLYPEPTIDE: Suc-Leu-Leu-Glu-Lys-Leu-Leu-Glu-O-HBB-Ser-Leu-Lys-NH$_2$ (SEQ ID NO: 20)

Prepare N$^\alpha$-Fmoc-O-TBDMS-Ser-Leu-N$^\epsilon$-Boc-Lys-Rink Resin (TBDMS attached to the side chain oxygen of a Serine residue) on an ABI430A peptide synthesizer using standard N$^\alpha$-Fmoc protection and HOBT active esters.

Treat N$^\alpha$-Fmoc-O-TBDMS-Ser-Leu-N$^\epsilon$-Boc-Lys-Rink Resin with acetic acid in tetrahydrofuran/water to give N$^\alpha$-Fmoc-Ser-Leu-N$^\epsilon$-Boc-Lys-Rink Resin.

Prepare N$^\alpha$-Fmoc-O-HBB-Ser-Leu-Ne-Boc-Lys-Rink Resin using standard Fmoc chemistry on an ABI430A peptide synthesizer from N$^\alpha$-Fmoc-Ser-Leu-Ne-Boc-Lys-Rink Resin and 3,5-di-t-butyl-4-hydroxybenzoic acid as N-hydroxybenzotriazole active ester (2 mmol acid, 4×excess active ester per each of two couplings).

Prepare Leu-Leu-Glu(Ot-Bu)-N$^\epsilon$-Boc-Lys-Leu-Leu-Glu (Ot-Bu)-O-HBB-Ser-Leu-N$^\epsilon$-Boc-Lys-Rink Resin (SEQ ID NO: 21) from N$^\alpha$-Fmoc-O-HBB-Ser-Leu-N$^\epsilon$-Boc-Lys-Rink Resin on an ABI430A peptide synthesizer using standard N$^\alpha$-Fmoc protection and HOBT active esters.

Couple Leu-Leu-Glu(Ot-Bu)-N$^\epsilon$-Boc-Lys-Leu-Leu-Glu (Ot-Bu)-O-HBB-Ser-Leu-N$^\epsilon$-Boc-Lys-Rink Resin (SEQ ID NO: 21) with succinic anhydride to give Suc-Leu-Leu-Glu (Ot-Bu)-N$^\epsilon$-Boc-Lys-Leu-Leu-Glu(Ot-Bu)-O-HBB-Ser-Leu-N$^\epsilon$-Boc-Lys-Rink Resin (SEQ ID NO: 22).

Cleave Suc-Leu-Leu-Glu(Ot-Bu)-N$^\epsilon$-Boc-Lys-Leu-Leu-Glu(Ot-Bu)-O-HBB-Ser-Leu-N$^\epsilon$-Boc-Lys-Rink Resin (SEQ ID NO: 22) from the resin and remove side chain protecting groups with trifluoroacetic acid, phenol, dimethylsulfide and water. Place under an argon atmosphere and stir for 1 hour. Evaporate the solvent in vacuo and purify by HPLC to give the title compound.

6(B). PREPARATION OF DPPC COMPLEX OF POLYPEPTIDE DESCRIBED IN EXAMPLE 6(A).

Peptide 6(A) is mixed with DPPC as described under Example 1(A).

EXAMPLE 7

7(A). PREPARATION OF POLYPEPTIDE: Suc-Leu-Leu-Glu-Lys-Leu-Leu-Glu-S-HBB-Cys-Leu-Lys-NH$_2$ (SEQ ID NO: 23)

Prepare Leu-Leu-Glu(Ot-Bu)-N$^\epsilon$-Boc-Lys-Leu-Leu-Glu (Ot-Bu)-Cys(SEt)-Leu-N$^\epsilon$-Boc-Lys-Rink Resin (SEQ ID NO: 24) Resin on an ABI430A peptide synthesizer using standard Na-Fmoc protection and HOBT active esters.

Couple Leu-Leu-Glu(Ot-Bu)-N$^\epsilon$-Boc-Lys-Leu-Leu-Glu (Ot-Bu)-Cys(SEt)-Leu-N$^\epsilon$-Boc-Lys-Rink Resin (SEQ ID NO: 24) with succinic anhydride to give Suc-Leu-Leu-Glu (Ot-Bu)-Ns-Boc-Lys-Leu-Leu-Glu(Ot-Bu)-Cys(SEt)-Leu-Ne-Boc-Lys-Rink Resin (SEQ ID NO: 25).

Mix Suc-Leu-Leu-Glu(Ot-Bu)-Ne-Boc-Lys-Leu-Leu-Glu (Ot-Bu)-Cys(SEt)-Leu-Ns-Boc-Lys-Rink Resin (SEQ ID NO: 25) (0.263 g), anhydrous dimethylformamide (5 mL) and methyl thioglycolate (450 μL). Stir under an argon atmosphere overnight to give Suc-Leu-Leu-Glu(Ot-Bu)-N$^\epsilon$-Boc-Lys-Leu-Leu-Glu(Ot-Bu)-Cys-Leu-N$^\epsilon$-Boc-Lys-Rink Resin (SEQ ID NO: 26).

Prepare Suc-Leu-Leu-Glu(Ot-Bu)-Ne-Boc-Lys-Leu-Leu-Glu(Ot-Bu)-S-HBB-Cys-Leu-N$^\epsilon$-Boc-Lys-Rink Resin (SEQ ID NO: 27) using standard Fmoc chemistry on an ABI430A peptide synthesizer from Suc-Leu-Leu-Glu(Ot-Bu)-N$^\epsilon$-Boc-Lys-Leu-Leu-Glu(Ot-Bu)-Cys-Leu-Ne-Boc-Lys-Rink Resin (SEQ ID NO: 26) and 3,5-di-t-butyl-4-hydroxybenzoic acid as N-hydroxybenzotriazole active ester (2 mmol acid, 4×excess active ester per each of two couplings).

Cleave Suc-Leu-Leu-Glu(Ot-Bu)-Ne-Boc-Lys-Leu-Leu-Glu(Ot-Bu)-S-HBB-Cys-Leu-N$^\epsilon$-Boc-Lys-Rink Resin (SEQ ID NO: 27) from the resin and remove side chain protecting groups with trifluoroacetic acid, phenol, dimethylsulfide and water. Place under an argon atmosphere and stir for 1 hour. Evaporate the solvent in vacuo and purify by HPLC to give the title compound.

7B. PREPARATION OF DPPC COMPLEX OF POLYPEPTIDE DESCRIBED IN EXAMPLE 7(A).

Peptide 7(A) is mixed with DPPC as described under Example 1(B).

EXAMPLE 8

8(A) PREPARATION OF POLYPEPTIDE: Suc-Leu-Leu-Glu-Lys-Leu-Leu-Glu-N$^\epsilon$-Trl-Lys-Leu-Lys-NH$_2$ (Trl-Lys-MAP10) (SEQ ID NO: 28)

The title compound is prepared according to the method described in Example 1 except that the target lysine residue is protected with 9-fluorinomethyloxycarbonyl (Fmoc). Prior to the addition of the next resudue, the N$^\epsilon$-Fmoc is removed with piperidine in dimethylformamide (DMF) and trl coupled via the preformed HOBT ester to the ε-amino group of lysine. The synthesis is continued with standard Boc chemistry, and the peptide cleaved, deprotected, and purified as described in Example 1.

PREPARATION OF DPPC COMPLEX OF POLYPEPTIDE IN EXAMPLE (A): Peptide 8(A) is mixed with DPPC as described under Example 1(B).

EXAMPLE 9

PREPARATION OF ANTIOXIDANT AMINO ACID DERIVATIVE: Fmoc-Glu[λ-HBB-ol ester]

Mix finely ground L-glutamic acid (2.0 g, 13.6 mmol) and anhydrous sodium sulfate (2.0 g) and 3,5-di-t-butyl-4-hydroxybenzyl alcohol (HBB-ol) (14 mmol)and tetrahydrofuran (75 mL). Add tetrafluoroboric acid etherate (54%, 3.7 mL, 27.2 mmol) and stir at room temperature for 15 hours. Filter and treat the filtrate with triethylamine (4.1 mL, 29.6 mmol) and evaporate the solvent in vacuo. Purify by chromatography to give Glu[λ-HBB-ol ester].

Dissolve Glu[λ-HBB-ol ester] (50 mmol) in 10% sodium carbonate solution (100 mL). Cool to 0° C. in an ice bath and add dioxane (50 mL), then slowly add, with stirring, a solution of 9-fluorenylmethyl chloroformate (13 g, 50.2 mmol) in dioxane (75 mL). Stir for 1 hour at 0° C. and 5 to 18 hours at room temperature. Pour the reaction mixture into 1.5 L ice-water. Extract with ether (2×400 mL) to remove unreacted chloroformate. Chill the aqueous phase in ice and acidify with concentrated hydrochloric acid to pH 2. Extract into ethyl acetate, wash with 0.1M hydrochloric acid and water. Dry (MgSO$_4$) and evaporate the solvent in vacuo to give N$^\alpha$-Fmoc-Glu[HBB-ol ester].

Incorporate into polypeptide on an ABI430A peptide synthesizer using standard $N^\alpha$-Fmoc protection and HOBT active esters.

EXAMPLE 10

PREPARATION OF ANTIOXIDANT AMINO ACID DERIVATIVE: $N^\alpha$-Fmoc-$N^\epsilon$-Boc-Lys[$N^\epsilon$-MBB-CH$_2$]

Mix $N^\alpha$-Fmoc-Lys (7.2 mmol) and 3,5-di-t-butyl-4-hydroxybenzaldehyde (HBB-al) (7.2 mmol) in acetonitrile (30 mL). Add sodium cyanoborohydride (1.37 g, 23.2 mmol). Add acetic acid as needed to maintain a slightly acidic medium. Stir for several hours, dilute with ethyl ether (100 mL) and wash with 1N sodium hydroxide. Separate the organic phase, dry (MgSO$_4$) and evaporate the solvent in vacuo to give $N^\alpha$-Fmoc-Lys[$N^\epsilon$-HBB-CH$_2$].

Dissolve $N^\alpha$-Fmoc-Lys[$N^\epsilon$-HBB-CH$_2$](10 mmol) in 50/50 dioxane/water (25 mL) and buffer to pH 10 with 1N sodium hydroxide. Add, by dropwise addition, an ether solution of t-butyl azidoformate (1.58 g, 11 mmol) at 10° C. Allow to warm to room temperature and buffer occasionally to retain pH 10. Acidify with a sodium citrate/citric acid buffer to pH 5, extract with ether (3×), dry (MgSO$_4$) and blow to a residue with a stream of nitrogen to give the title compound.

Incorporate into polypeptide on an ABI430A peptide synthesizer using standard $N^\alpha$-Fmoc protection, HOBT active esters and Rink Resin.

The following antioxidant starting materials may be used as described in the preceding examples.

EXAMPLE 11

PREPARATION OF STARTING MATERIAL ANTIOXIDANT COMPOUND: 3-t-Butyl-5-methyl-4-hydroxybenzoic acid Charge a reaction vessel with a suspension of sodium hydride (4.74 g, 0.198 mol) in anhydrous ethylene glycol dimethyl ether (150 mL). Add, by dropwise addition, a solution of 2-t-butyl-6-methylphenol (0.1 mol) in ethylene glycol dimethyl ether (150 mL). Warm to 50°–60° C. for 1.5 hours then introduce carbon dioxide through a gas-disparging tube below the surface of the reaction mixture for 20 hours. Cool to 5° C. and destroy the excess sodium hydride carefully with methyl alcohol (30 mL). After hydrogen evolution ceases, adjust the pH of the reaction mixture to 2 with 1N hydrochloric acid. Dilute with water (1.6 L) and collect the title compound by filtration.

EXAMPLE 12

PREPARATION OF STARTING MATERIAL ANTIOXIDANT COMPOUND: (6-Hydroxy-7-t-butyl-5-isopropyl-8-propylchroman-2-yl)acetic acid Mix magnesium turnings (45 mg, 1.85 mmol) and 1-chloro-2,2-dimethylpropane (74.6 mg, 0.7 mmol) in anhydrous ether (9 mL). Heat and stir vigorously, then add, by dropwise addition, 1,2-dibromoethane (156 mg, 0.839 mmol) in anhydrous ether (1.5 mL). Reflux for 12 hours, place under an argon atmosphere and cool to 0°–5° C. Add, by dropwise addition, a solution of isobutyryl chloride (0.533 mmol) in anhydrous diethyl ether (1.5 mL). Stir at 0°–5° C. for 1.5 hours, pour into a mixture of ice and concentrated hydrochloric acid (0.15 mL) and separate the organic phase. Wash with ethyl acetate, 5% aqueous sodium carbonate and brine. Dry (MgSO$_4$) and evaporate the solvent in vacuo to give 2,2,6-trimethyl-4-heptanone.

Dissolve vinylmagnesium chloride (0.7 mmol) in anhydrous diethyl ether (1 mL), place under an argon atmosphere and cool to 1°–5° C. Add, by dropwise addition, a solution of butyryl chloride (0.533 mmol) in anhydrous diethyl ether (1.5 mL). Stir at 0°–5° C. for 1.5 hours, pour into a mixture of ice and concentrated hydrochloric acid (0.15 mL) and separate the organic phase. Wash with water, 5% aqueous sodium carbonate and brine. Dry (MgSO$_4$) and evaporate the solvent in vacuo to give propyl vinyl ketone.

Dissolve 2,2-6-trimethyl-4-heptanone (0.4 mol) in methanol (10 mL) and add potassium tert-butoxide (12 g. 0.1 mol). Add, by dropwise addition, a solution of propyl vinyl ketone (0.2 mol) in methanol (10 mn). Stir for 10 minutes and partion between ethyl ether and brine. Separate the organic phase and wash with brine until neutral. Dry (Na$_2$SO$_4$) and evaporate the solvent in vacuo to give 2-propyl-3-t-butyl-5-isopropylbenzoquinone.

Dissolve 2-propyl-3-t-butyl-5-isopropylbenzoquinone (10 mmol), 1,1,3,3-tetramethyldisiloxane (1.79 mL, 10 mmol) and iodine (0.05 g) in methylene chloride (30 mL). Stir at reflux for 30 minutes and extract with 1N sodium hydroxide (30 mL). Acidify the aqueous phase with concentrated hydrochloric acid and extract into ethyl acetate (4×10mL), dry (Na$_2$SO$_4$) and evaporate the solvent in vacuo to give 2-propyl-3-t-butyl-4-hydroxy-5-isopropylphenol.

Dissolve 2-propyl-3-t-butyl-4-hydroxy-5-isopropylphenol (2.0 mol) and trimethyl orthoformate (0.3 L) in methanol (1.2 L) and degas. Place under a nitrogen atmosphere and cool to 3° C. and add concentrated sulfuric acid (5 mL). Add, by dropwise addition, methyl vinyl ketone (340 mL, 4.0 mol) and stir without cooling for 44 hours. Pour into aqueous sodium hydrogen caronate and extract into ethyl ether. Dry (MgSO$_4$) and evaporate the solvent in vacuo to give 2-methoxy-2-methyl-7-t-butyl-5-isopropyl-8-propyl-chroman-6-ol.

Dissolve 2-methoxy-2-methyl-7-t-butyl-5-isopropyl-8-propyl-chroman-6-ol (2 mol) in pyridine (600 mL) and add acetic anhydride (900 mL). Degas and stir under a nitrogen atmosphere for 18 hours. Pour into ice/water and stir for 3 hours. Extract into ethyl ether, dry (MgSO$_4$), evaporate the solvent in vacuo and purify by chromatography to give 2-methoxy-2-methyl-7-t-butyl-5-isopropyl-8-propyl-chroman-6-yl-acetate.

Dissolve 2-methoxy-2-methyl-7-t-butyl-5-isopropyl-8-propyl-chroman-6-yl-acetate (2 mol) in acetone (2.5 L) and add water (2 L) followed by concentrated hydrochloric acid (16.6 mL). Distil the solvent from the stirred mixture until the head temperature reaches 90° C. Cool the suspension, dilute with ethyl ether and wash with aqueous sodium hydrogen carbonate. Dry (MgSO$_4$), evaporate the solvent in vacuo and purify by chromatography to give 2-hydroxy-2-methyl-7-t-butyl-5-isopropyl-8-propyl-chroman-6-yl-acetate.

Suspend sodium hydride (47.2 g of 56% in mineral oil, 1.10 mol) in anhydrous tetrahydrofuran (1 L). Place under a nitrogen atmosphere and add, by dropwise addition, trimethyl phosphonoacetate (209.4 g, 1.15 mol). Stir the 25 minutes and add a solution of 2-hydroxy-2-methyl-7-t-butyl-5-isopropyl-8-propyl-chroman-6-yl-acetate (0.5 mol) in tetrahydrofuran (1 L). Stir at room temperature for 18 hour then heat at reflux for 4 hours. Cool, evaporate the solvent in vacuo and purify by chromatography to give the title compound.

BIOLOGICAL

Methods of testing the synthetic surfactant preparations for efficacy are well known in the art. For example, the synthetic surfactant preparations of the present invention can be tested in any appropriate manner such as in the adult rat lung model (Ikegami, et al., (1979) *Pediatr. Res.* 13, 777–780).

Pressure-volume characteristics of surfactant-depleted rat lungs are similar to those of lungs of infants with hyaline membrane disease and restoration of the pressure-volume relationship of the lung to normal is related to the amount of surfactant instilled in a dose dependent manner. (Bermel, M. S., et al., Lavaged excised rat lungs as a model of surfactant deficiency, *Lung* 162:99–113 (1984)).

EXAMPLE 13

Isolated Rat Lavaged Lung Model. The experimental procedures for animal preparation, pressure-volume curve registration and lung lavage were adapted from those described by Ikegami et al., *Pediatr. Res.* 11:178–182 (1977) and *Pediatr. Res.* 13:777–780 (1979, and Bermel et al, *Lung* 162:99–113 (1984). Male Sprague Dawley rats (200–250 g) were anesthetized with sodium pentobarbital and exsanguinated. The trachea was cannulated and the thoracic organs were removed en bloc. After removal of the adventitious tissue, the trachea and lungs (~2 g) were suspended in saline (0.9%), placed in a vacuum chamber, and degassed according to the procedure of Stengel et al. the degassed lungs were suspended in saline in a 37° C., jacketed reservoir and the tracheal cannula was connected both to a water manometer and a glass syringe by a T-tube. The glass syringe was placed in an infusion/withdrawal pump. Lungs were rapidly inflated with air to 30 cm $H_2O$ pressure at the rate of 10 ml/min to minimize air trapping, and were maintained at this pressure for 10 min by intermittently adding air to the lungs. The total volume of air infused was recorded as the total lung capacity (TLC) which was generally 14–15 ml. The lungs were then deflated at a rate of 2.5 ml/min until zero pressure was attained. During deflation, pressure was read from the water manometer at 1 cm intervals and recorded. These data were used to construct a pressure-volume (P-V) or quasi-static compliance curve after correction for the P-V curve of the apparatus. After degassing and equilibration, the lungs were rendered surfactant-deficient by repeated lavage with 5 ml/g lavage buffer (0.9% NaCl, 10 mM HEPES, pH 7.4). The procedures of degassing, equilibrating, and lavaging were repeated (15–20 times) until the pressure-volume curve had become distinctly sigmoidal in shape and the volume of air remaining in the lungs at 5 cm $H_2O$ pressure was less than or equal to 3 ml. At this point, the lungs were considered surfactant-deficient. For testing, 2 ml of 0.9% NaCl, 10 mM HEPES buffer, pH 7.4, were added to the dry lung surfactants (25 mg of phospholipid; 100–125 mg/kg) and the mixture was vortexed, flushed with nitrogen and incubated for 1 h at 45° C. The mixture was then vortexed again, degassed if foamy, and 2 ml of the test mixture were introduced into and withdrawn from the lungs four times by syringe. When the test mixture was reintroduced to the lungs for the fifth time, it was allowed to remain in the lungs. This procedure was adopted to encourage even distribution of the material throughout the lung. The lungs were degassed, allowed to equilibrate at 37° C. for 5 min, and a P-V measurement was performed. Lungs were studied while supported in saline at 37° C. as opposed to ambient temperature since the physical characteristics of the surfactants may be dependent upon temperature. Canine lung surfactant was administered in a similar manner except that the surfactant was heated for only 5 min. Data are presented in terms of the %TLC. The deflation limbs of the pressure-volume (P-V) curves in adult rat lungs were analyzed by calculating the total lung capacities (%TLC) at 5 and 10 cm $H_2O$ pressure ($PC_5$ and $PC_{10}$). Comparisons were based on per cent restoration=($PC_{5 (sufficient)}$−$PC_{5 (test)}$)×100/($PC_{5 (sufficientP}$−$PC_{5 (deficient)}$) and made by one-way analysis of variance using the general linear models procedure with specific contrasts of the means (SAS Institute Inc., Cary, N.C.). A probability value of <0.05 was taken to indicate statistical significance. Lavage and treatment with test mixtures did not produce a change in the absolute TLC of greater than 6%.

Antioxidant Activity. Peptides were dissolved in trifluoroethanol (TFE) and mixed with soy phosphatidyl-choline (PC) in chloroform. After drying under a $N_2$ stream, the mixture was resuspended in ethanol and injected into buffer (50 mM NaCl, 50 mM Tris-HCl, pH 7.0) to obtain a final concentration of 0.5 mM phospholipid. Peroxidation was initiated with 50 µM $Fe^{2+}$ plus a mixture of 50 µM $Fe^{3+}$ and 250 µM histidine. At intervals over a period of 15 min at 37° C., 1 mL samples of the reaction mixture were taken for determination of TBARs (thiobarbituric acid reactive substances). Two mL of a mixture of 2 parts of 0.67% thiobarbituric acid/0.05N NaOH and 1 part of 10% trichloroacetic acid and 0.05 mL of 2% butylated hydroxytoluene were added. Reaction proceeded for 30 min at 100° C. The tubes were then cooled, centrifuged for 15 min at 3000 rpm and transferred to acrylic cuvettes. The differences in absorbance at 532 nm and 700 nm (to correct for light scattering) were measured and the TBARs were calculated in units of malondialdehyde equivalents using a molar extinction coefficient of $1.56 \times 10^5$ $M^{-1}$ $cm^{-1}$.

CD Spectra. Circular dichroic (CD) spectra of samples in 1 mm circular cuvettes were recorded at room temperature on a Jasco J-500A Spectropolarimeter with 2 nm slit width. The CD spectrum of buffer was subtracted from the CD spectrum of the sample after each scan. The scan rate is 2 nm/min and the time constant was 8 sec. Data was collected at 0.04 nm intervals and averaged over a 0.2 nm interval.

Surface Tension Measurements. The minimum and maximum surface tension of an oscillating bubble were measured on samples at 37° C. with a cycle rate of 20 per min in a pulsating bubble surfactometer (PBS, Electronetics Corp.), essentially as described by Enhorning, *J. Appl. Physiol* 43:198–203 (1977). The plastic cample chamber was rinsed with a dilute solution of dishwashing detergent, thoroughly rinsed with water and dried under a stream of $N_2$ prior to use.

Results

The structures of the test peptides are shown in FIG. 1. WMAP10 is an effective amphipathic α-helical peptide tested in DPPC as a synthetic lung surfactant. The peptide analogs HBB-Lys-MAP10, HBS-Cys-MAP10 and Trl-Lys-MAP10 incorporate a hydrophobic antioxidant. The Trolox was coupled to Lys in Trl-LysMAP10 to form two isomers, Trolox(I)-MAP10 and Trolox(II)-MAP10 which were separated but the stereochemistry was not identified. The structures of the peptides were compared by CD spectroscopy in water and in trifluoroethanol which promotes hydrogen-bonding and the formation of α-helical structure. The CD spectra are shown in FIG. 2. The calculated secondary structures are in Table I. All of the peptides were highly α-helical in TFE and less so in water. Little difference in the α-helical content of the peptides in TFE is evident from the data in Table I. However, substantial differences are observed in water.

TABLE I

Conformation of peptides based on CD spectra

| Peptide | water α | water β | TFE α | α |
|---|---|---|---|---|
| WMAP10 | 64 | 0 | 73 | 0 |
| HBB-LysMAP10 | 59 | 4 | 78 | 0 |
| HBS-CysMAP10 | 55 | 21 | 89 | 0 |
| Trolox(I)-MAP10 | 26 | 39 | 78 | 0 |
| Trolox(II)-MAP10 33 | 33 | 20 | 89 | 0 |

*Data were fit to the standard spectra of Greenfield & Fasman, Biochemistry 8: 4108–4116 (1969). Fits are all ±3% (SEM of fit).

The physical properties of the lung surfactant mixtures were evaluated by differential scanning calorimetry (DSC) and in the pulsating bubble surfactometer. The enthalpy of the phase transition of the DPPC is markedly reduced in lung surfactant mixtures containing peptides which strongly interact with lipid (McLean, L. R. et al., *Biochemistry* 30:31–37 (1991)) and are effective in the rat lavaged lung model. The enthalpies and phase transition temperatures are in Table II. In addition, a significant decrease in the minimum surface tension ($\gamma_{min}$) in a pulsating bubble was observed for all of the synthetic lung surfactant mixtures. Probucol slightly increased $\gamma_{min}$ (Table II).

TABLE II

Physical Properties of Lung Surfactant Mixtures

| Mixture | γmin (mN/m) |
|---|---|
| DPPC* | 38 |
| +WMAP10 | <2 |
| +WMAP10 + probucol | 12 |
| +HBS-LysMAP10 | <2 |
| +HBS-CysMAP10 | 2 |
| +Trolox(I)-MAP10 | 10 |
| +Trolox(II)-MAP10 | 2 |

*Values for DPPC were measured on unsonicated liposomes.
γmin values are after 10 min of pulsing.

Figure 3A:
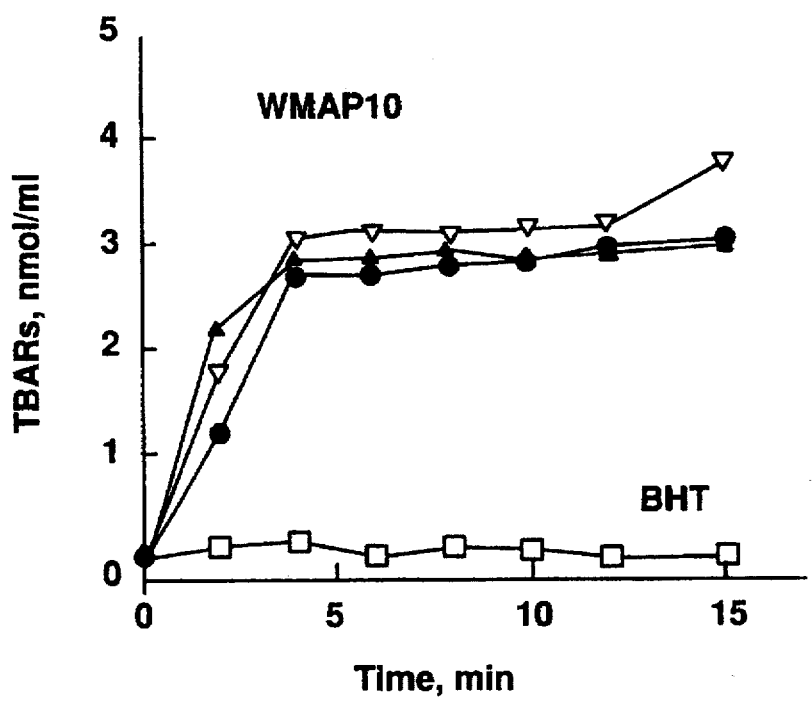
FIG. 3 shows inhibition of lipid peroxidation by peptides and peptide antioxidants. (●) control in all panels; WMAP 10 panel: (□) BHT (Butylhydroxytoluene) (1 µg/mL), (▽) 1.5% (1.5 parts peptide:100 parts DPPC), (▼) 4.5%; HBB-LysMAP10 panel; (∇) 0.6%, (▼) 1.2%, (□) 2.4%, (■) 3.6%, (△) 4.8%; HBS-CysMAP10 panel: (∇) 0.4%, (■) 0.8%, (▼) 1.5%, (□) 3%.
Figure 3B:
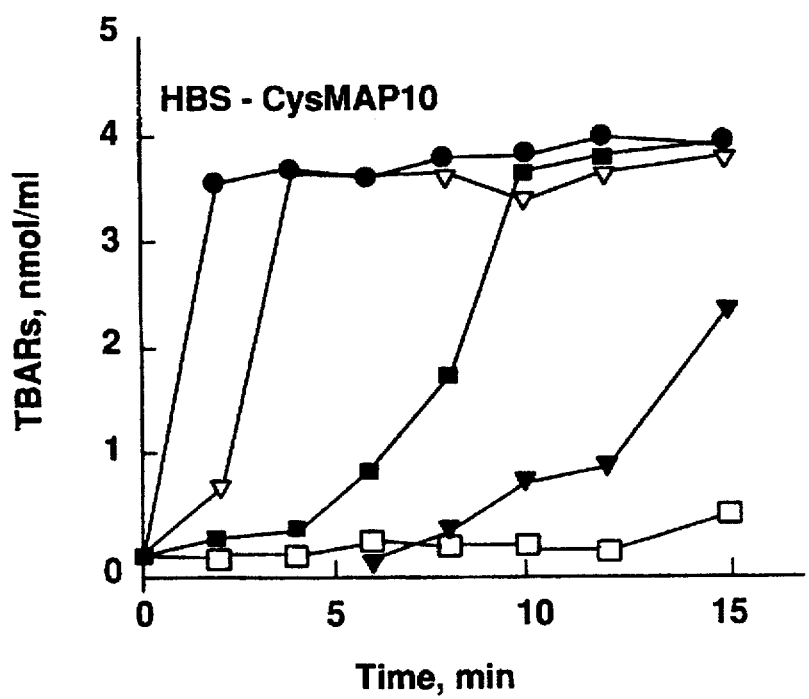
Figure 3C:
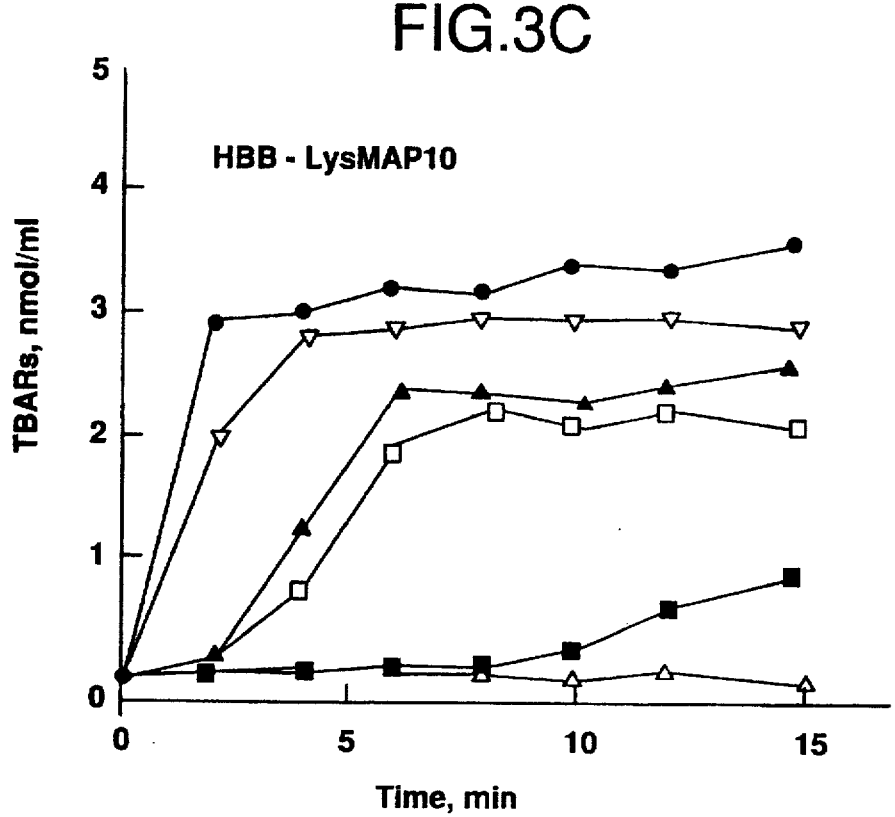
Figure 4:
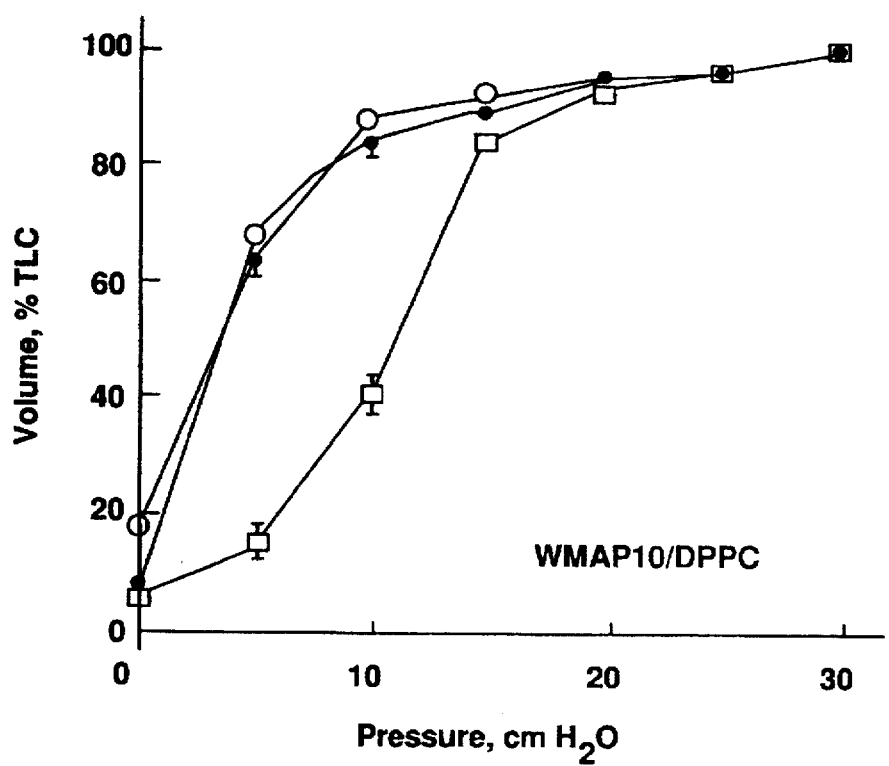
FIG. 4 shows representative pressure-volume deflation curves for the indicated surfactant mixtures (●). The curves without points correspond to the fully sufficient lung (leftmost curve) and the deficient, lavaged lung (right-most curve).

The efficacy of the peptides as antioxidants was compared with that of probucol added to mixtures of WMAP10 in soy PC mixtures. BHT was tested as a control. WMAP10 in soy PC had no antioxidant activity in the range examined (FIG. 3). Nor did an analog containing Lys in place of the Trp residue (data not shown). Probucol totally inhibits oxidation for at least 8 min at a concentration of 0.6% (by weight) (data not shown). Both the HBB-Lys and HBS-Cys derivatives were effective antioxidants at concentrations similar to that used for preparation of the synthetic surfactants. The Trolox derivatives were also effective antioxidants in similar mixtures (data not shown).

The preparations administered to the rat had a translucent appearance. The deflation limb of the pressure-volume (P-V) curve in adult rat lungs was analyzed by calculation of the per cent of total lung capacity (TLC) at 5 cm $H_2O$ pressure ($PC_5$) and the TLC at 10 cm $H_2O$ ($PC_{10}$). The restoration based upon the $PC_5$ values was used to compare the test mixtures. DPPC alone had no significant effect on the pressure-volume (P-V) curves of the lavaged lung. For the synthetic surfactants, peptide concentrations of either 2 or 4 weight % were chosen based on the optimal concentration for WMAP10 mixtures with DPPC (MAP10). The results are summarized in Table III. The WMAP10 sequence is highly effective in restoring the P-V curve of the lavaged adult rat lung to near sufficiency when mixed with DPPC. Addition of probucol or substitution of peptides containing the HBB or Trolox functional group does not diminish the activity of the peptide-DPPC mixtures.

TABLE III

Efficacy of synthetic surfactants in the adult rat lavaged lung model

| Mixture | Dose (mg) | n | $PC_5$ (% TLC) | $PC_{10}$ (% TLC) | restoration* (%) |
|---|---|---|---|---|---|
| sufficient | | 50 | 68 ± 1 | 87 ± 1 | 100 |
| deficient | | 50 | 17 ± 1 | 45 ± 1 | 0 |
| DPPC | | 4 | 13 ± 1 | 31 ± 2 | −11 ± 8 |
| +2% WMAP10 | 10 | 3 | 54 ± 4 | 79 ± 3 | 75 ± 8 |
| +2% WMAP10 + probucol | 10 | 3 | 62 ± 7 | 82 ± 5 | 87 ± 11 |
| +2% WMAP10 | 25 | 3 | 63 ± 3 | 84 ± 2 | 92 ± 3 |
| +4% WMAP10 | 10 | 3 | 63 ± 5 | 84 ± 4 | 95 ± 11 |
| +4% HBB-LysMAP10- | 25 | 3 | 68 ± 2 | 83 ± 1 | 94 ± 3 |
| +2% HBS-CysMAP10 | 25 | 2 | 62 ± 3 | 84 ± 2 | 104 ± 4 |
| +2% Trolox(I)-MAP10 | 25 | 3 | 61 ± 4 | 84 ± 1 | 103 ± 7 |
| +2% Trolox(II)-MAP10 | 25 | 3 | 63 ± 3 | 85 ± 1 | 100 ± 5 |

*Restorations are based on PC5 and compared to sufficient and deficient measurements on the same lungs as used for the test material. Values are mean ±SEM. The probucol concentration was 2% by weight.

What is claimed is:

1. A mixture comprising a peptide and a lipid, or a peptide and a mixture of lipids wherein said peptide has the formula:

$$X\text{-}Y\text{-}Z\text{-}Y'\text{-}Q\ 1$$

or a pharmaceutically acceptable salt or optically active isomer thereof, wherein:

X is hydrogen, a $C_{1-5}$ alkyl group, a $C_{1-10}$ acyl group, an amino acid, dipeptide or tripeptide;

Y and Y' are each independently a bond, -(Ser)n- where n is an integer of from 1 to 3, or T, wherein T is:

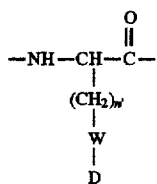

n' is an integer from 1–8; W is —NHC(O)—, —NHCH$_2$—, —C(O)O— —OC(O)—, —SC(O)—, or —SS—; and D is:

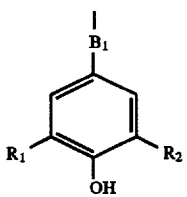  Da or

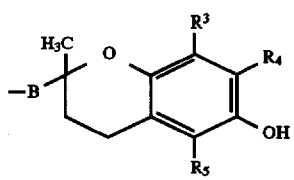  Db wherein B is a bond, C$_{1-16}$ alkylene, or C$_{2-16}$ alkenylene, and B$_1$ is B or

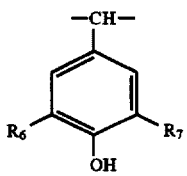

wherein each R$_1$, R$_2$, R$_3$, R$_4$, R$_5$, R$_6$ and R$_7$ is independently a C$_{1-6}$ alkyl;

or X and Y together are Da-C(O)— or Db-C(O)—;

Q is hydroxy, amino, alkylamino, alkoxy group, —O-Da, or —O-Db;

Z is a peptide residue of from 8 to 25 amino acid residues consisting of a fragment of the oligomer having the sequence

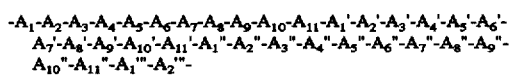

and which begin with any one of the amino acid residues designated A$_1$–A$_{11}$ wherein A$_1$, A$_1$', A$_1$", A$_1$''', A$_4$, A$_4$', A$_4$", A$_8$, A$_8$', and A$_8$" are each independently selected from The group of hydrophilic amino acid residues consisting of -Glu-, -Asp-, -Ala-, -Gln-, -Asn-, -Gly-, -Ser-, -Thr-, -Lys-, -Arg-, -Orn-, and -hArg-;

A$_2$, A$_2$', A$_2$", A$_2$''', A$_3$, A$_3$', A$_3$", A$_6$, A$_6$', A$_6$", A$_7$, A$_7$', A$_7$", A$_{10}$, A$_{10}$', and A$_{10}$" are each independently selected from the group of lipophilic amino acid residues consisting of -Leu-, -Nle-, -Met-, -Ala-, -Val-, -Phe-, -Nva-, -Ile-, and -Tyr-, or amino acid residue derivative T;

A$_5$, A$_5$', A$_5$", A$_{11}$, A$_{11}$', and A$_{11}$" are each independently selected from the group of basic amino acid residues consisting of -Lys-, -Orn-, -Arg-, or hArg-;

A$_9$, A$_9$', A$_9$" are each independently selected from the group of lipophilic, neutral or basic amino acid residues consisting of -Leu-, -Nle-, -Met-, -Ala-, -Val-, -Phe-, -Nva-, -Ile-, -Tyr-, -Thr-, -Ser-, -Gln-, -Ash-, -,Sly-, -Lys-, -Arg-, -hArg-, -Trp-, -Orn-, -Trp(For)-, or amino acid residue derivative T;

with the proviso that there is at least one T, —O-Da, O-Db, Da-C(O) or Db-C(O)— in formula 1; and said lipid or mixture of lipids is selected from the group consisting of DPPC, PC, CL, PG, PS, FA and TG.

2. A mixture of claim 1 wherein DPPC comprises the major component of the lipid.

3. A mixture of claim 1 wherein the lipid is a mixture of DPPC and PG.

4. A mixture of claim 1 wherein the lipid consists of from about 85–100% DPPC and from about 0–15% PG.

5. A mixture of claim 1 wherein the polypeptide is Suc-Leu-Leu-Glu-Lys-Leu-Leu-Glu-Leu-Lys-NH$_2$ (SEQ ID NO: 32).

6. A mixture of claim 1 wherein the polypeptide is Suc-Leu-Leu-Glu-Lys-Leu-Leu-Glu-Leu-Lys-NH$_2$ (SEQ ID NO: 33).

7. A mixture of claim 1 wherein the polypeptide is Suc-Leu-Leu-Glu-Lys-Leu-Leu-Glu-Leu-Lys-NH$_2$ (SEQ ID NO: 34).

8. A mixture of claim 1 wherein the amino acids of the polypeptide have the D isomer configuration.

9. A method of treating respiratory distress syndrome in a subject in need thereof which comprises administering to the subject an effective amount of a mixture comprising a peptide and a lipid, or a peptide and a mixture of lipids wherein said peptide has the formula:

X-Y-Z-Y'-Q  1 or a pharmaceutically acceptable salt or optically active isomer thereof, wherein:

X is hydrogen, a C$_{1-5}$ alkyl group, a C$_{1-10}$ acyl group, an amino acid, dipeptide or tripeptide;

Y and Y' are each independently a bond,

-(Set)n- where n is an integer of from 1 to 3, or T, wherein T is:

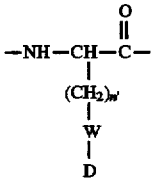

n' is an integer from 1–8; W is —NHC(O)—, —NHCH$_2$—, —C(O)O— —OC(O)—, —SC(O) —, or —SS—; and D is:

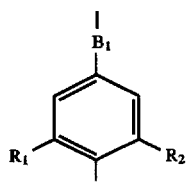
Da or

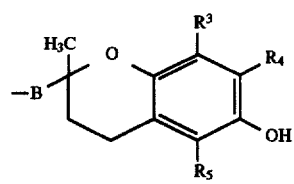
Db wherein B is a bond, $C_{1-16}$ alkylene, or $C_{2-16}$ alkenylene, and $B_1$ is B or

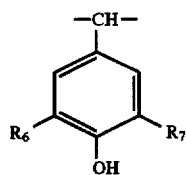

wherein each $R_1$, $R_2$, $R_3$, $R_4$, $R_5$, $R_6$ and $R_7$ is independently a $C_{1-6}$ alkyl;

or X and Y together are Da-C(O)— or Db-C(O)—;

Q is hydroxy, amino, alkylamine, alkoxy group, —O-Da, or —O-Db;

Z is a peptide residue of from 8 to 25 amino acid residues consisting of a fragment of the oligomer having the sequence

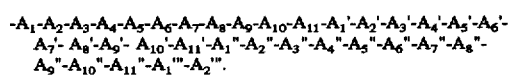

and which begins with any one of the amino acid residues designated $A_1$–$A_{11}$ wherein $A_1$, $A_1'$, $A_1''$, $A_1'''$, $A_4$, $A_4'$, $A_4''$, $A_8$, $A_8'$, and $A_8''$ are each independently selected from the group of hydrophilic amino acid residues consisting of -Glu-, -Asp-, -Ala-, -Gln-, -Asn-, -Gly-, -Ser-, -Thr-, -Lys-, -Arg-, -Orn-, and -hArg-;

$A_2$, $A_2'$, $A_2''$, $A_2'''$, $A_3$, $A_3'$, $A_3''$, $A_6$, $A_6'$, $A_6''$, $A_7$, $A_7'$, $A_7''$, $A_{10}$, $A_{10}'$, and $A_{10}''$ are each independently selected from the group of lipophilic amino acid residues consisting of -Leu-, -Nle-, -Met-, -Ala-, -Val- -Phe- -Nva- -Ile- and -Tyr-, or amino acid residue derivative T;

$A_5$, $A_5'$, $A_5''$, $A_{11}$, $A_{11}'$, and $A_{11}''$ are each independently selected from the group of basic amino acid residues consisting of -Lys-, -Orn-, -Arg-, or hArg-;

$A_9$, $A_9'$, $A_9''$ are each independently selected from the group of lipophilic, neutral or basic amino acid residues consisting of -Leu-, -Nle-, -Met-, -Ala-, -Val-, -Phe-, -Nva-, -Ile-, -Tyr-, -Thr-, -Ser-, -Gln-, -Asn-, -Gly-, -Lys-, -Arg-, -hArg-, -Trp-, -Orn-, -Trp(For)-, or amino acid residue derivative T;

with the proviso that there is at least one T, —O-Da, O-Db, Da-C(O) or Db-C(O)— in formula 1; and said lipid or mixture of lipids is selected from the group consisting of DPPC, PC, CL, PG, PS, FA and TG.

10. A method of claim 9 wherein DPPC comprises the major component of the lipid.

11. A method of claim 9 wherein the lipid is a mixture of DPPC and PG.

12. A method of claim 9 wherein the lipid consists of from about 85–100% DPPC and from about 0–15% PG.

13. A method of claim 9 wherein the peptide is Suc-Leu-Leu-Glu-Lys-Leu-Leu-Glu-Leu-Lys-NH$_2$ (SEQ ID NO: 32).

14. A method of claim 9 wherein the polypeptide is Suc-Leu-Leu-Glu-Lys-Leu-Leu-Glu-Leu-Lys-NH$_2$ (SEQ ID NO: 33).

15. A method of claim 9 wherein the peptide is Suc-Leu-Leu-Glu-Lys-Leu-Leu-Glu-Leu-Lys-NH$_2$ (SEQ ID NO: 37).

16. A method of claim 9 wherein the amino acids of the peptide are of the D-configuration.

* * * * *

UNITED STATES PATENT AND TRADEMARK OFFICE
CERTIFICATE OF CORRECTION

PATENT NO. : 5,683,982

DATED : November 4, 1997

INVENTOR(S) : Larry R. McLean, et al.

It is certified that error appears in the above-identified patent and that said Letters Patent is hereby corrected as shown below:

Column 3, Line 22 Patent reads "acids residues" and should read -- acid residues --.
Column 3, Line 22 Patent reads "$A_1 - A_{12}$" and should read -- $A_1 - A_{11}$ -- .
Column 4, Line 25 Patent reads "glyycine" and should read -- glycine -- .
Column 4, Line 39 Patent reads "all D configuration or all L configuration" and should read -- all D configurations or all L configurations -- .
Column 9, Line 41 Patent reads "sysnthesizer" and should read -- synthesizer -- .
Column 10, Line 27 Patent reads "Ns" and should read -- $N^\epsilon$ --.
Column 10, Line 28 Patent reads "Nεprotecting" and should read -- $N^\epsilon$ protecting --.
Column 14, Line 47 Patent reads " i(A) " and should read -- 1(A) --.
Column 15, Line 49 Patent reads " - L S - " and should read -- Lys -- .
Column 15, Line 51 Patent reads "Ns" and should read -- $N^\epsilon$ --.
Column 15, Line 64 Patent reads "Ns" and should read -- $N^\epsilon$ --.
Column 16, Line 6 Patent reads " L s 3 5 " and should read -- -Lys-3,5 -- .
Column 16, Line 13 Patent reads "Ne" and should read -- $N^\epsilon$ --.
               Line 16 Patent reads "Ne" and should read -- $N^\epsilon$ --.
               Line 17 Patent reads "Ne" and should read -- $N^\epsilon$ --.
               Line 21 Patent reads "Ne" and should read -- $N^\epsilon$ --.
               Line 33 Patent reads "Ne" and should read -- $N^\epsilon$ --.
               Line 47 Patent reads "Ne" and should read -- $N^\epsilon$ --.
               Line 66 Patent reads "Ne" and should read -- $N^\epsilon$ --.
               Line 67 Patent reads "Ne" and should read -- $N^\epsilon$ --.
Column 17, Line 63 Patent reads "Ne" and should read -- $N^\epsilon$ --.
               Line 65 Patent reads "Ne" and should read -- $N^\epsilon$ --.
Column 18, Line 5 Patent reads "Ne" and should read -- $N^\epsilon$ --.
               Line 9 Patent reads "Ne" and should read -- $N^\epsilon$ --.
               Line 14 Patent reads "Ne" and should read -- $N^\epsilon$ --.
Column 19, Line 9 Patent reads "MBB" and should read -- HBB -- .
Column 20, Line 14 Patent reads "(10mn)" and should read -- (10mL) -- .

UNITED STATES PATENT AND TRADEMARK OFFICE
CERTIFICATE OF CORRECTION

PATENT NO.  :  5,683,982

DATED        :  November 4, 1997

INVENTOR(s) :  Larry R. McLean et al

It is certified that error appears in the above-identified patent and that said Letters Patent is hereby corrected as shown below:

Column 20, Line 33 Patent reads "caronate" and should read -- carbonate -- .
Column 20, Line 47 Patent reads "Distil" and should read - --Distill --.
Column 20, Line 59 Patent reads "buty-" and should read -- butyl -- .
Column 20, Line 60 Patent reads "18 hour" and should read -- 18 hours --.
Column 39, Line 61 Patent reads "The" and should read -- the -- .
Column 40, Line 11 Patent reads " -Ash-, -,Sly -," and should read -- -Asn-, -Gly-, --.
Column 41, Line 43 Patent reads "alkylamine" and should read -- alkylamino -- .
Column 42, Line 36 Patent reads "polypeptide" and should read --peptide --.

Signed and Sealed this

Fifteenth Day of May, 2001

Attest:

NICHOLAS P. GODICI

Attesting Officer    Acting Director of the United States Patent and Trademark Office